(12) United States Patent
Hayes et al.

(10) Patent No.: US 6,989,377 B2
(45) Date of Patent: Jan. 24, 2006

(54) TREATING VITAMIN D RESPONSIVE DISEASES

(75) Inventors: Colleen E. Hayes, Madison, WI (US); Faye E. Nashold, Sun Prairie, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 10/170,746

(22) Filed: Jun. 13, 2002

(65) Prior Publication Data

US 2003/0109506 A1 Jun. 12, 2003

Related U.S. Application Data

(63) Continuation-in-part of application No. PCT/US00/34913, filed on Dec. 21, 2000, and a continuation-in-part of application No. 09/469,985, filed on Dec. 21, 1999, now Pat. No. 6,358,939.

(51) Int. Cl.
C07C 401/00 (2006.01)
A61K 31/59 (2006.01)

(52) U.S. Cl. .................................. 514/167; 552/653
(58) Field of Classification Search ................ 514/167; 552/653
See application file for complete search history.

(56) References Cited

U.S. PATENT DOCUMENTS

| | | | |
|---|---|---|---|
| 4,312,806 A | 1/1982 | Lambert et al. | |
| 4,638,043 A | 1/1987 | Szycher et al. | |
| 5,216,002 A | 6/1993 | Gidda et al. | |
| 5,238,931 A | 8/1993 | Yoshikawa et al. | |
| 5,294,630 A | 3/1994 | Blake et al. | |
| 5,368,854 A | 11/1994 | Rennick | |
| 5,391,555 A | 2/1995 | Marshall et al. | |
| 5,446,035 A | 8/1995 | Neef et al. | |
| 5,506,213 A | 4/1996 | Carson et al. | |
| 5,518,725 A | * 5/1996 | Daynes et al. | 424/212.1 |

(Continued)

FOREIGN PATENT DOCUMENTS

| | | |
|---|---|---|
| DE | 44 05 545 | 8/1995 |
| EP | 0927721 | 12/1997 |
| WO | WO 96/30326 | 10/1996 |
| WO | WO 98/51644 | 11/1998 |
| WO | WO 98/51678 | 11/1998 |
| WO | WO 01/42205 | 6/2001 |

OTHER PUBLICATIONS

Barrat et al. (DN 136339213, CAPLUS, abstract of J. of Experimental Medicine (2002), 195(5), 603–616).*

Penna et al. (DN 132:292680, CAPLUS, abstrct of J. of immunology (2000), 164(5): 2405–2411).*

Dam et al. (DN 132:146376, CAPLUS, abstract of J. of investigative Dermatology (1999), 113(6), 1082–1089).*

DeLuca, Hector et al., "Vitamin D: Its Role and Uses in Immunology," *The FASEB Journal,* 2001, vol. 15, pp. 2579–2585.

Breese, E. et al., "Interleukin–2– and interferon–gamma–secreting T cells in normal and diseased human intestinal mucosa," *Immunology,* 1993, vol. 78, pp. 127–131.

(Continued)

*Primary Examiner*—Sabiha N. Qazi
(74) *Attorney, Agent, or Firm*—Foley & Lardner LLP

(57) ABSTRACT

The present invention relates to therapeutics for the prevention and treatment of vitamin D responsive diseases in humans, as well as other animals, through the use of biologically active vitamin D compounds in combination with at least one other immunomodulatory compound such as interleukin-10, interleukin-4, or a TNFα inhibitor.

20 Claims, 3 Drawing Sheets

U.S. PATENT DOCUMENTS

| | | | |
|---|---|---|---|
| 5,552,439 A | 9/1996 | Panetta | |
| 5,569,680 A | 10/1996 | Wu | |
| 5,583,125 A * | 12/1996 | Steinmeyer et al. | 514/167 |
| 5,643,602 A | 7/1997 | Ulmius | |
| 5,663,157 A | 9/1997 | Steinmeyer et al. | |
| 5,710,142 A | 1/1998 | Calverley et al. | |
| 5,711,964 A | 1/1998 | Dattagupta et al. | |
| 5,716,945 A | 2/1998 | Grue-Sorensen | |
| 5,716,946 A | 2/1998 | DeLuca et al. | |
| 5,756,449 A | 5/1998 | Andersen et al. | |
| 5,756,733 A | 5/1998 | Hesse et al. | |
| 5,786,347 A | 7/1998 | Hesse et al. | |
| 5,792,795 A | 8/1998 | Buser et al. | |
| 5,811,562 A | 9/1998 | Hesse et al. | |
| 5,824,313 A | 10/1998 | Daynes et al. | |
| 5,830,505 A | 11/1998 | Fischer et al. | |
| 5,834,016 A | 11/1998 | Naeff et al. | |
| 5,834,021 A | 11/1998 | Speirs | |
| 5,851,548 A | 12/1998 | Dattagupta et al. | |
| 5,872,140 A | 2/1999 | Hesse et al. | |
| 5,876,746 A | 3/1999 | Jona et al. | |
| 5,877,168 A | 3/1999 | Miyamoto et al. | |
| 5,883,271 A | 3/1999 | Ono | |
| 5,888,969 A | 3/1999 | Girten et al. | |
| 5,889,028 A | 3/1999 | Sandborn et al. | |
| 5,891,865 A | 4/1999 | DeLuca et al. | |
| 5,902,806 A | 5/1999 | Ikeda et al. | |
| 5,905,074 A | 5/1999 | Schneider | |
| 5,929,056 A | 7/1999 | Mourino et al. | |
| 5,932,214 A | 8/1999 | Lobb et al. | |
| 5,932,565 A | 8/1999 | Grue-Sorensen | |
| 5,936,105 A | 8/1999 | Paaren | |
| 5,952,317 A | 9/1999 | Deluca et al. | |
| 5,981,597 A * | 11/1999 | Wu | 514/616 |
| 6,214,373 B1 | 4/2001 | Snowden | |
| 6,358,939 B1 * | 3/2002 | Hayes et al. | 514/167 |
| 6,440,953 B1 | 8/2002 | DeLuca et al. | |
| 2003/0188756 A1 * | 10/2003 | Cantorna | 128/898 |

OTHER PUBLICATIONS

Best, W. R. et al., "Development of a Crohn's Disease Activity Index: National Cooperative Crohn's Disease Study," Gastroenterology, 70(3); pp. 439–444 (1976); published by The Williams & Wilkins Co.

Bradford, M. M., A Rapid and Sensitive Method for the Quantitation of Microgram Quantities of Protein Utilizing the Principle of Protein–Dye Binding, Anal. Biochem., 72; pp. 248–254 (1976).

Schefler, W. C., Statistics for the Biological Sciences, $2^{nd}$ Ed., pp. 214–216; p. A–17 (1979); published by Addison–Wesley Publ. Co., Reading, MA, USA.

Moolenbeek, C. et al., "The 'Swiss roll': a simple technique for histological studies of the rodent intestine," Lab. Anim., 15; pp. 57–59 (1981).

Krawisz, J. E. et al., "Quantitative Assay for Acute Intestinal Inflammation Based on Myeloperoxidase Activity," Gastroenterology, 87; pp. 1344–1350 (1984); published by the American Gastroenterological Association.

Koizumi et al., "Effects of Corticosteroid and 1,24R–Dihydroxy–Vitamin $D_3$ Administration on Lymphoproliferation and Autoimmune Disease in MRL/MP–Ipr/Ipr Mice," Int. Archs Allergy appl. Immun., 77; pp. 396–404 (1985); published by S. Karger AG, Basel.

Ostrem, V.K. et al., "24– and 26–homo–1,25–dihydroxyvitamin $D_3$: Preferential activity in inducing differentiation of human leukemia cells HL–60 in vitro," Proc. Natl. Acad. Sci. USA, 84; pp. 2610–2614, May (1987).

Pallone et al., "Activation of peripheral blood and intestinal lamina propria lymphocytes in Crohn's disease. In vivo state of activation and in vitro response to stimulation as defined by the expression of early activation antigens," Gut, 28; pp. 745–753 (1987).

Kaulfersch et al., "Polyclonal Nature of the Intestinal Mucosal Lymphocyte Populations in Inflammatory Bowel Disease," Gastroenterology, 95; pp. 364–370 (1988); published by the American Gastroenterological Association.

Abe et al., "A Synthetic Analogue of Vitamin $D_3$, 22–OXA–1α, 25–Dihydroxyvitamin $D_3$, is a Potent Modulator of in vivo Immuno–Regulating Activity Without Inducing Hypercalcemia in Mice," Endocrinology, 124(5); pp. 2645–2647 (1989); published by The Endocrine Society.

Norman, A. W., et al., "Structure–Function Studies on Analogues of 1α,25–Dihydroxyvitamin $D_3$: Differential Effects on Leukemic Cell Growth, Differentiation, and Intestinal Calcium Absorption," Cancer Res., 50; pp. 6857–6864, Nov. 1 (1990).

Okayasu, I. et al., A Novel Method in the Induction of Reliable Experimental Acute and Chronic Ulcerative Colitis in Mice, Gastroenterology, 98; pp. 694–702 (1990); published by the American Gastroenterological Association.

Perlman, K. et al., 4–Homologated 1,25–Dihydroxyvitamin $D_3$ Compounds: Separation of Calcium and Cell Differentiation Activities, Biochemistry, 29(1); pp. 190–196 (1990).

Sonnenberg, A. et al., "Epidemiology of Inflammatory Bowel Disease Among U.S. Military Veterans," Gastro., 101; pp. 122–130 (1991); published by the American Gastroenterological Association.

Sonnenberg, A. et al., "Geographic Variation of Inflammatory Bowel Disease Within the United States," Gastro., 100; pp. 143–149 (1991); published by the American Gastroenterological Association.

Uno, H., "Hokuku," Nippon Jui Chikusan Daigaku Keukya, 40; pp. 111–112 (1991).

Binderup, L., "Immunological Properties of Vitamin D Analogues and Metabolites," Biochemical Pharmacology, 43(9); pp. 1885–1892 (1992); published by Pergamon Press Ltd, Great Britain.

Bouillon, R. et al., "Structure Function Analysis of Vitamin D Analogs with C–ring Modifications*," J. Biol. Chem., 267(5); pp. 3044–3051 (1992); published by The American Society of Biochemistry and Molecular Biology, Inc.

Labuda, M. et al., "Two Hereditary Defects Related to Vitamin D Metabolism Map to the Same Region of Human Chromosome 12q13–14,", J. Bone Min. Res., 7(12); pp. 1447–1453 (1992); published by Mary Ann.

Lemire, J.M. et al., "Protolongation of the Survival of Murine Cardiac Allografts by the Vitamin $D_3$ Analogue 1,25–Dihydroxy–$\Delta^{16}$–Cholecalciferol," Transplantation, 54(4); pp. 762–763, Oct. (1992).

Lillevang, S. T. et al., "Single and combined effects of the vitamin D analogue KH1060 and cyclosporin A on mercuric–chloride–induced autoimmune disease in the BN rat," Clin. Exp. Immunol., 88; pp. 301–306 (1992).

Schull, M. M. et al., "Targeted disruption of the mouse transforming growth factor–β1 gene results in multifocal inflammatory disease," Nature, 359; p. 693–699, Oct. 22 (1992).

Sonnenberg, A. et al., "Geography and Inflammatory Bowel Disease," *Gastroenterol.*, 102; p. 1827 (1992).

Breese, E. et al., "Interleukin–2– and interferon–γ–secreting T cells in normal and diseased human intestinal mucosa," *Immunology*, 78; pp. 127–131 (1993).

Kühn, R. et al., "Interleukin–10–Deficient Mice Develop Chronic Enterocolitis," *Cell*, 75; pp. 263–274, Oct. 22 (1993); published by Cell Press.

Mombaerts, P. et al., "Spontaneous Development of Inflammatory Bowel Disease in T Cell Receptor Mutant Mice," *Cell*, Oct. 22; 75(2); pp. 275–282 (1993); published by Cell Press.

Motley, R. J. et al., "A four–year longitudinal study of bone loss in patients with inflammatory bowel disease," *Bone and Mineral*, 23; pp. 95–104 (1993); published by Elsevier Scientific Publishers Ireland Ltd.

Sadlack, B. et al., "Ulcerative Colitis–like Disease in Mice with a Disrupted Interleukin–2 Gene," *Cell*, 75; pp. 253–261, Oct. 22 (1993); published by Cell Press.

Strober, W. et al., "Chronic Intestinal Inflammation: An Unexpected Outcome in Cytokine of T Cell Receptor Mutant Mice," *Cell*, 75; pp. 203–205, Oct. 22 (1993); published by Cell Press.

Veyron, P. et al., "Two novel vitamin D analogues, KH 1060 and CB 966, prolong skin allograft survival in mice," *Transplant Immunol.*, 1(1); pp. 72–76 (1993); published by Edward Arnold.

Lemire, J. M. et al., "1/25–Dihydroxy–24–OXO–16ene–Vitamin D3, a renal metabolite of the vitamin D analog 1,25–dihydroxy–16ene–vitamin D3, exerts immunosuppressive activity equal to its parent without causing hypercalcemia *in vivo*," *Endocrinology*, 135(6); pp. 2818–2821 (1994); published by The Endocrine Society.

Bouillon, R. et al., "Structure–Function Relationships in the Vitamin D Endocrine System," *Endocr. Rev.*, Apr., 16(2); pp. 200–257 (1995); published by The Endocrine Society.

Elson, C. O. et al., "Experimental Models of Inflammatory Bowel Disease," *Gastroenterology*, 109; pp. 1344–1367 (1995); published by the American gastroenterological Association.

Holick, M.F., "Environmental factors that influence the cutaneous production of vitamin $D^{1-3}$," *Am. J. Clin. Nutr.*, Mar., 61 (3 Suppl.); pp. 638S–645S (1995); published by American Society for Clinical Nutrition.

Powrie, F., "T Cells in Inflammatory Bowel Disease: Protective and Pathogenic Roles," *Immunity*, 3; pp. 171–174, Aug. (1995); published by Cell Press.

Saitoh, O. et al., "Intestinal Protein Loss and Bleeding Assessed by Fecal Hemoglobin, Transferrin, Albumin, and Alpha–1–Antitrypsin Levels in Patients with Colorectal Diseases," *Digestion*, 56; pp. 67–75 (1995); published by S. Karger AG, Basel.

Targan, S. R. et al., "Clarifying the causes of Crohn's," *Nature Medicine*, 1(12); pp. 1241–1243, Dec. (1995).

Berg, D. J. et al., "Enterocolitis and Colon Cancer in Interleukin–10–deficient Mice Are Associated with Aberrant Cytokine Production and CD4+ TH1–like Responses," *J. Clin. Invest.*, 98(4); pp. 1010–1020 (1996); published by The American Society for Clinical Investigation, Inc.

Bouillon, R. et al., "Nonhypercalcemic Vitamin D Analogs: Interactions with the Vitamin D–Binding Protein," *Horm. Res.*, 45; pp. 117–121 (1996); published by S. Karger AG, Basel.

Caccavo, D. et al., "Two Spatially Distant Epitopes of Human Lactoferrin," *Hybridoma*, 15(4); pp. 263–269 (1996); published by Mary Ann Liebert, Inc.

Cantorna, M. T. et al., "1,25–Dihydroxyvitamin $D_3$ reversibly blocks the progression of relapsing encephalomyelitis, a model of multiple sclerosis," *Proc. Natl. Acad. Sci. USA*, 93; pp. 7861–7864, Jul. (1996).

Danzé, P–M et al., "Association of HLA class II genes with susceptibility to Crohn's disease," *Gut*, 39; pp. 69–72 (1996).

Davidson, N. J. et al., "T Helper Cell 1–type CD4+ T Cells, but Not B Cells, Mediate Colitis in Interleukin 10–deficient Mice," *J. Exp. Med.*, 184; pp. 241–251 (1996); published by The Rockefeller University Press.

Hugot, J.–P. et al., "Mapping of a susceptibility locus for Crohn's disease on chromosome 16," *Nature*, 79; pp. 821–823, Feb. 29 (1996).

MacDermott, R. P., "Alterations of the mucosal immune system in inflammatory bowel disease," *J. Gastroenterology*, 31; pp. 907–916 (1996); published by Springer–Verlag.

Moum, B. et al., "Incidence of Ulcerative Colitis and Indeterminate Colitis in Four Counties of Southeastern Norway, 1990–93," *Scand. J. Gastroenterol.*, 31; pp. 362–366 (1996).

Powrie, F. et al., "A Critical Role for Transforming Growth Factor–β but Not Interleukin 4 in the Suppression of T Helper Type 1–mediated Colitis by $CD45RD^{low}$ CD4+ T Cells," *J. Exp. Med.*, 183; pp. 2669–2674, Jun. (1996); published by The Rockefeller University Press.

Satsangi, J. et al., "Two stage genome–wide search in inflammatory bowel disease provides evidence for susceptibility loci on chromosomes 3, 7 and 12," *Nature Genetics*, 14; pp. 199–202, Oct. (1996)

Schneider, T. et al., Quantiation of eosinophil and neutrophil infiltration into rat lung by specific assays for eosinophil peroxidase and myeloperoxidase—Application of a Brown Norway rat model of allergic pulmonary inflammation, *J. of Immun. Methods*, 198; pp. 1–14 (1996); published by Elsevier Science B.V.

Shivananda, S. et al., "Incidence of inflammatory bowel disease across Europe: is there a difference between north and south? Results of the European collaborative study on inflammatory bowel disease (EC–IBD)," *Gut*, 39; pp. 690–697 (1996).

Sugi, K. et al., Fecal Lactoferrin as a Marker for Disease Activity in Inflammatory Bowel Disease: Comparison with Other Neutrophil–derived Proteins, *Am. J. Gastroenterol.*, 91(5); pp. 927–934 (1996); published by Am. Coll. of Gastroenterology.

Andreassen, H. et al., "Inflammatory Bowel Disease and Osteoporosis," *Scand. J. Gastroenterol.*, 32; pp. 1247–1255 (1997).

Chan, F. K. W. et al., "Differential Diagnosis, Causes, and Management of Hypercalcemia," *Cur. Prob. Surgery*, 34(6); pp. 445–523, Jun. (1997); published by Mosby–Year Book, Inc., St. Louis, Missouri.

Dwarakanath, A. D. et al., "Differential excretion of leucocyte granule components in inflammatory bowel disease: implications for pathogenesis," *Clin. Sci.*, 92; pp. 307–313 (1997).

Groux, H. et al., "A CD4+ T–cell subset inhibits antigen–specific T–cell responses and prevents colitis," *Nature*, 389; pp. 737–742, Oct. 16 (1997).

Haussler, M. R. et al., "The vitamin D hormone and its nuclear receptor: molecular actions and disease states," *J. Endocrinol.,* 154; pp. 557–573 (1997); published by Journal of Endocrinology Ltd., Great Britain.

Hogaboam, C. M. et al., "Therapeutic Effects of Interleukin–4 Gene Transfer in Experimental Inflammatory Bowel Disease," *J. Clin. Invest.,* 100(11); pp. 2766–2776, Dec. (1997); published by The American Society for Clinical Investigation, Inc.

King, C. C. et al., "Secretion and inactivation of myeloperoxidase by isolated neutrophils," *J. of Leukocyte Biology,* 61; pp. 293–302, Mar. (1997).

Kornbluth, A. et al., "Cyclosporin for Severe Ulcerative Colitis: A User's Guide," *Amer. J. of Gastro.,* 92(9); pp. 1424–1428 (1997); published by Am. Coll. Of Gastroenterology.

Monteleone, G. et al., "Interleukin 12 is Expressed and Actively Released by Crohn's Disease Intestinal Lamina Propria Mononuclear Cells," *Gastroenterol.,* 112; pp. 1169–1178 (1997); published by the American Gastroenterological Association.

Radhakrishnan, S. et al., "Ulcerative Colitis in Oman—A Prospective Study of the Incidence and Disease Pattern from 1987 to 1994," *Digestion,* 58; pp. 266–270 (1997); published by S. Karger AG, Basel.

Robinson, M., "Optimizing Therapy for Inflammatory Bowel Disease," *Amer. J. of Gastro.,* 92(12); pp. 12S–17S (1997); published by Am. Coll. Of Gastroenterology.

Romagnani, P. et al., "T cells and cytokines in Crohn's disease," *Cur. Opin. In Immunology,* 9; pp. 793–799 (1997); published by Current Biology Ltd.

Sartor, R. B., "Pathogenesis and Immune Mechanisms of chronic Inflammatory Bowel Diseases," *AJG,* 92(12); pp. 5S–11S, December Suppl. (1997); published by Am. Coll. Of Gastroenterology.

Strober, W. et al., Reciprocal IFN–$\gamma$ and TGF–$\beta$ responses regulate the occurrence of mucosal inflammation, *Immunol. Today,* 18(2); pp. 61–64, Feb. (1997); published by Elsevier Science Ltd.

Targan, S. R. et al., "A Short–Term Study of Chimeric Monoclonal Antibody cA2 to Tumor Necrosis Factor $\alpha$ for Crohn's Disease," *New England Journal of Medicine,* 337(15); pp. 1029–1035, Oct. 9 (1997).

Asou, H. et al., "19–nor Vitamin–D Analogs: A New Class of Potent Inhibitors of Proliferation and Inducers of Differentiation of Human Myeloid Leukemia Cell Lines," *Blood,* 92(7); pp. 2441–2449, Oct. 1, (1998).

Boot, A. M. et al., "Bone mineral density and nutritional status in children with chronic inflammatory bowel disease," *Gut,* 42; pp. 188–194 (1998).

Bregenholt, S. et al., "Increased intracellular Th1 cytokines in scid mice with inflammatory bowel disease," *Eur. J. Immunol.,* 28; pp. 379–389 (1998); published by Wiley–VCH Verlag GmbH, D–69451 Weinheim.

Cantoma, M. T. et al., "1,25–Dihydroxyvitamin $D_3$ Is a Positive Regulator for the Two Anti–Encephalitogenic Cytokines TGF–$\beta$1 and IL–4[1]," *J. Immunol.,* 160; pp. 5314–5319 (1998); published by the American Association of Immunologists.

Cantoma, M. T. et al., "1,25–Dihydroxycholecalciferol Inhibits the Progression of Arthritis in Murine Models of Human Arthritis[1,2]," *J. Nutr.,* 128; pp. 68–72 (1998); published by American Society for Nutritional Sciences.

Cantoma, M. T. et al., "1,25–Dihydroxyvitamin $D_3$ Prolongs Graft Survival Without Compromising Host Resistance to Infection or Bone Mineral Density," *Transplantation,* 66(7); pp. 828–831, Oct. 15 (1998); published by Williams & Wilkins.

Cong, Y. et al., "CD4[+] T Cells Reactive to Enteric Bacterial Antigens in Spontaneously Colitic C3H/HeJBir Mice: Increased T Helper Cell Type 1 Response and Ability to Transfer Disease," *J. Exp. Med.,* 187(6); pp. 855–864, Mar. 16 (1998); published by The Rockefeller University Press.

Davidson, N. J. et al., "IL–12, But Not IFN–$\gamma$, Plays a Major Role in Sustaining the Chronic Phase of Colitis in IL–10–Deficient Mice," *J. Immunol.,* 161; pp. 3143–3149 (1998); published by The American Association of Immunologists.

Duerr, R. H. et al., "Linkage and Association between Inflammatory Bowel Disease and a Locus on Chromosome 12," *Am. J. Hum. Genet.,* 63; pp. 95–100 (1998); published by The American Society of Human.

Fiocchi, C., "Inflammatory Bowel Disease: Etiology and Pathogenesis," *Gastroenterology,* 115; pp. 182–205 (1998); published by the American Gastroenterological Association.

Fort, M. M. et al., "A Role for NK Cells as Regulators of CD4[+] T Cells in a Transfer Model of Colitis," *J. Immunol.,* 161; pp. 3256–3261 (1998); published by The American Association of Immunologists.

Mahler, M. et al., "Differential susceptibility of inbred mouse strains to dextran sulfate sodium–induced colitis," *Am. J. Physiol.,* 274 (*Gastro & Liver Physiol 37*); pp. G544–G551 (1998); published by the American Physiological Society.

Sandler, R. S. et al., "The Incidence of IBD is Higher in the North," *Inflamm. Bowel Dis.,* 4(2); pp. 175–176, May (1998).

Satsangi, J. et al., "Genetics of inflammatory bowel disease," *Clin. Sci.,* 94; pp. 473–478, May (1998).

Sellon, R. K. et al., "Resident Enteric Bacteria Are Necessary for Development of Spontaneous Colitis and Immune System Activation in Interleukin–10–Deficient Mice," *Infect. and Immun.,* 66(11); pp. 5224–5231 (1998); published by American Society for Microbiology.

Thomas, M.K. et al., "Hypovitaminosis D in Medical Inpatients," *N. Eng. J. Med.,* 338(12); pp. 777–783 (1998); published by the Massachusetts Medical Society.

Bhan, A. K. et al., "Colitis in transgenic and knockout animals as models of human inflammatory bowel disease," *Immunol. Reviews,* 169; pp. 195–207 (1999); published by Munksgaard, Denmark.

Boehm, M. F. et al., "Novel nonsecosteroidal vitamin D mimics exert VDR–modulating activities with less calcium mobilization than 1,25–dihydroxyvitamin $D_3$," *Chemistry & Biology,* 6; pp. 265–275, May (1999); published by Elsevier Science Ltd.

Cantoma, M. T. et al., "Dietary Calcium is a Major Factor in 1,25–Dihydroxycholecalciferol Suppression of Experimental Autoimmune Encephalomyelitis in Mice," *J. Nutr.,* 129; pp. 1966–1971 (1999); published by American Society for Nutritional Sciences.

Tada, M. et al., (DN BA81:48751, BIOSIS, abstract of J. Jpn. Soc. COLO–PROCTOL, (1985), 38 (6), 663–668).

Berniss, C. J. et al., "Interleukin–2 is one of the targets of 1,25–dihydroxyvitamin D3 in the immune system," *Archives of Biochemistry and Biophysics,* 402 (2002), pp. 249–254; published by Elesevier Science (USA).

Bickston, S.J. et al., "Recombinant Interleukin 10 for the Treatment of Active Crohn's Disease: Lessons in Biologic Therapy," *Gastroenterology*, 119 (6) (2000), pp. 1781–1783; published by American Gastroenterological Association (USA).

Cantoma, M. T. et al., "1,25–Dihydroxycholecalciferol Prevents and Ameliorates Symptoms of Experimental Murine Inflammatory Bowel Disease," *J. Nutr.*, 130 (2000), pp. 2648–2652; published by American Society for Nutritional Sciences (USA).

Colombel, J–F. et al., "Interleukin 10 (Tenovil) in the prevention of postoperative recurrence of Crohn's disease," *Gut*, 49 (2001) pp. 42–46; published by British Medical Association (United Kingdom).

Cornillie, F. et al., "Infliximab induces potent anti–inflammatory and local immunomodulatory activity but no systemic immune suppression in patients with Crohn's disease," *Aliment Pharmacol Ther.*, 15 (2001), pp. 463–473; published by Blackwell Science Ltd.

Fedorak, R. N. et al., "Recombinant Human Interleukin 10 in the Treatment of Patients with Mild to Moderately Active Crohn's Disease," *Gastroenterology*, 119 (2000), pp. 1473–1482; published by American Gastroenterological Association (USA).

Fedorak, R. N. et al., "Human Recombinant Interleukin–10 is Safe and Well Tolerated but Does Not Induce Remission in Steroid Dependent Crohn's Disease," *Gastroenterology*, 120 (Supp. 1) (2001), p. A–127; published by W. B. Saunders (Philadelphia, USA).

Hanauer, S. B. et al., "Evolving Treatment Strategies for Inflammatory Bowel Disease," *Annu. Rev. Med.*, 52 (2001), pp. 299–318; published by Annual Reviews.

Karn, L. Y. et al., "TNF–$\alpha$ antagonists for the treatment of Crohn's disease," *Exp. Opin. Pharmacother.*, 1 (4) (2000), pp. 615–622; published by Ashley Publication Ltd.

Puchner, Thomas C. et al., "Successful Desensitization and Therapeutic Use of Infliximab in Adult and Pediatric Crohn's Disease Patients with Prior Anaphylactic Reaction," *Inflamm. Bowel Dis.*, 7 (1) (2001), pp. 34–37; published by Crohn's & Colitis Foundation of America, Inc. (USA).

Ricart, E. et al., "Infliximab for Crohn's Disease in Clinical Practice at the Mayo Clinic: The First 100 Patients," *Am. J. of Gastroenterology*, 96 (3) (2001), pp. 722–729; published by Am. Coll. Of Gasstroenterology (USA).

Sandborn, W.J. et al., "An Engineered Human Antibody to TNF (CDP571) for Active Crohn's Disease: A Randomized Double–Blind Placebo–Controlled Trial," *Gastroenterology*, 120 (2001), pp. 1330–1338; published by American Gastroenterological Association.

Sandborn, W. J. et al., "Etanercept for Active Crohn's Disease: A Randomized, Double–Blind, Placebo–Controlled Trial," *Gastroenterology*, 121 (5) (2001), pp. 1088–1094; published by American Gastroenterological Association (USA).

Sands, B. E. et al., "Infliximab in the Treatment of Severe, Steroid–Refractor Ulcerative Colitis: A Pilot Study," *Inflamm. Bowel Dis.*, 7 (2) (2001), pp. 83–88; published by Crohn's & Colitis Foundation of America, Inc. (USA).

Schreiber, S. et al., "Safety and Efficacy of Recombinant Human Interleukin 10 in Chronic Active Crohn's Disease," *Gastroenterology*, 119 (6) (2000), pp. 1461–1472; published by American Gastroenterological Association (USA).

Schreiber, S. et al., "Immunoregulatory role of Interleukin 10 in Patients With Inflammatory Bowel Disease," *Gastroenterology*, 108 (5) (1995), pp. 1434–1444; published by American Gastroenterological Association (USA).

Stio, M. et al., "Suppressive effect of 1,25–dihydroxyvitamin $D_3$ and its analogues EB 1089 and KH 1060 on T lymphocyte proliferation in active ulcerative colitis," *Biochemical Pharmacology*, 61 (2001), pp. 365–371; published by Elsevier Science Inc.

Targan, S. R., "Biology of inflammation in Crohn's disease: Mechanisms of action of anti–TNF–$\alpha$ therapy," *Can. J. Gastroenterology*, 14 (Suppl. C) (2000), pp. 13C–16C.

van Berge Henegouwen, G. P., ["Consensus for infliximab treatment of patients with Crohn's disease"], *Ned Tijdschr. Geneeskd.*, 144 (38) (2000), pp. 1844–1845 (Netherlands). English Abstract is provided on page 1845 of the reference.

van Deventer. S. J. et al., "Multiple Doses of Intravenous Interleukin 10 in Steroid–Refractory Crohn's Disease," *Gastroenterology*, 113 (2) (1997), pp. 383–389; published by American Gastroenterological Association (USA).

Harries, A.D. et al., "Vitamin D status in Crohn's disease: association with nutrition and disease activity," *Gut*, 26 (1985), pp. 1197–1203.

Issenman, R. M., "Bone Mineral Metabolism in Pediatric Inflammatory Bowel Disease," *Inflamm. Bowel Dis.*, 5 (3) (1999), pp. 192–199; published by Crohn's & Colitis Foundation of America, Inc. (USA).

Jahnsen, J. et al., "Vitamin D Status, Parathyroid Hormone and Bone Mineral Density in Patients with Inflammatory Bowel Disease," *Scand. J. Gastroenterol.*, 37 (2002), pp. 192–199; published by Taylor & Francis.

Kirchgatterer, A. et al., "Examination, Prevention and Treatment of Osteoporosis in Patients with Inflammatory Bowel Disease: Recommendations and Reality," *Acta Medica Austriaca*, 29 (2002), pp. 120–123; U.S. Copyright Clearance Center Code Statement: 0303–8173/2002/2904–0120.

Lamb, E. J. et al., "Metabolic bone disease is present at diagnosis in patients with inflammatory bowel disease," *Aliment Pharmacol. Ther.*, 16 (2002), pp. 1895–1902; published by Blackwell Science Ltd.

Scharla, S. H. et al., "Bone mineral density and calcium regulating hormones in patients with inflammatory bowel disease (Crohn's disease and ulcerative colitis)," *Exp. Clin. Endocrinol.*, 102 (1994), pp. 44–49; published by Johann Ambrosius Barth.

Schulte, C. et al., "Reduced Bone Mineral Density and Unbalanced Bone Metabolism in Patients with Inflammatory Bowel Disease," *Inflamm. Bowel Dis.*, 4 (4) (1998), pp. 268–275; published by Crohn's & Colitis Foundation of America, Inc. (USA).

Silvennoinen, J., "Relationships between vitamin D, parathyroid hormone and bone mineral density in inflammatory bowel disease," *J. Intern. Med.*, 239 (2) (1996), pp. 131–137; published by Blackwell Science Ltd.

Sonnenberg, A. et al., "25–Hydroxycholecalciferol Serum Levels in Patients with Crohn's Disease," *Acta Hepato–Gastroenterol.*, 24 (1977), pp. 293–295; published by Georg Thieme Verlag Stuttgart (Germany).

Vogelsang, H. et al., "Bone Disease in Vitamin D–Deficient Patients with Crohn's Disease," *Digestive Diseases and Sciences*, 34 (7) (1989); pp. 1094–1099; published by Plenum Publishing Corporation (USA).

Vogelsang, H. et al., "25–Hydroxyvitamin D. absorption in patients with Crohn's disease and with pancreatic insufficiency," *Wien Klin Wochenschr.*, 109 (17) (1997), pp. 678–682; published by Springer–Verlag (Austria).

* cited by examiner

1α,25-dihydroxyvitamin D₃

19-nor-1α,25-dihydroxyvitamin D₂

24-homo-22-dehydro-22E-
1α,25-dihydroxyvitamin D₃

19-nor-21-epi-1α,25-dihydroxyvitamin D₃

1,25S-(OH)₂-16,23-diene-
26-F₃-19-nor D₃

KH1060

LG190090

LG190119

LG190155

LG190176

LG190178

TREATING VITAMIN D RESPONSIVE DISEASES

This application is a continuation-in-part of and claims priority to international application PCT/US/00/34913, filed on Dec. 21, 2000, designating the United States of America, and published on Jun. 28, 2001, in the English language in accordance with PCT Article 21(2) as WO 01/46132, and is a Continuation-in-part of and which claims priority to U.S. patent application Ser. No. 09/469,985, filed on Dec. 21, 1999, and now U.S. Pat. No. 6,358,939. International application PCT/US/00/34913 and U.S. patent application Ser. No. 09/469,985, now U.S. Pat. No. 6,358,939, are herein incorporated by reference.

The present application was funded in part with government support under grant number R43-DK56568, from the National Institutes of Health. The government has certain rights in this invention.

FIELD OF THE INVENTION

The present invention relates to therapeutics for the prevention and treatment of vitamin D responsive diseases in humans, as well as other animals, through the use of biologically active vitamin D compounds in combination with at least one other immunomodulatory compound such as interleukin-10 (IL-10), interleukin-4 (IL-4), or a TNFα inhibitor.

BACKGROUND OF THE INVENTION

Inflammatory bowel diseases (IBD) are defined by chronic, relapsing intestinal inflammation of obscure origin. IBD refers to two distinct disorders, Crohn's disease and ulcerative colitis (UC). Both diseases appear to involve either a dysregulated immune response to GI tract antigens, a mucosal barrier breach, and/or an adverse inflammatory reaction to a persistent intestinal infection. The GI tract luminal contents and bacteria constantly stimulate the mucosal immune system, and a delicate balance of proinflammatory and anti-inflammatory cells and molecules maintains the integrity of the GI tract, without eliciting severe and damaging inflammation [MacDermott, R. P., *J. Gastroenterology*, 31:907–916 (1996)]. It is unknown how the IBD inflammatory cascade begins, but constant GI antigen-dependent stimulation of the mucosal and systemic immune systems perpetuates the inflammatory cascade and drives lesion formation.

There is no known cure for IBD, which afflicts 2 million Americans. Current methods of managing IBD symptoms cost an estimated $1.2 billion annually in the United States alone.

In patients with IBD, ulcers and inflammation of the inner lining of the intestines lead to symptoms of abdominal pain, diarrhea, and rectal bleeding. Ulcerative colitis occurs in the large intestine, while in Crohn's, the disease can involve the entire GI tract as well as the small and large intestines. For most patients, IBD is a chronic condition with symptoms lasting for months to years. It is most common in young adults, but can occur at any age. It is found worldwide, but is most common in industrialized countries such as the United States, England, and northern Europe. It is especially common in people of Jewish descent and has racial differences in incidence as well. The clinical symptoms of IBD are intermittent rectal bleeding, crampy abdominal pain, weight loss and diarrhea. Diagnosis of IBD is based on the clinical symptoms, the use of a barium enema, but direct visualization (sigmoidoscopy or colonoscopy) is the most accurate test. Protracted IBD is a risk factor for colon cancer. The risk for cancer begins to rise significantly after eight to ten years of IBD.

Some patients with UC only have disease in the rectum (proctitis). Others with UC have disease limited to the rectum and the adjacent left colon (proctosigmoiditis). Yet others have UC of the entire colon (universal IBD). Symptoms of UC are generally more severe with more extensive disease (larger portion of the colon involved with disease).

The prognosis for patients with disease limited to the rectum (proctitis) or UC limited to the end of the left colon (proctosigmoiditis) is better then that of full colon UC. Brief periodic treatments using oral medications or enemas may be sufficient. In those with more extensive disease, blood loss from the inflamed intestines can lead to anemia, and may require treatment with iron supplements or even blood transfusions. Rarely, the colon can acutely dilate to a large size when the inflammation becomes very severe. This condition is called toxic megacolon. Patients with toxic megacolon are extremely ill with fever, abdominal pain and distention, dehydration, and malnutrition. Unless the patient improves rapidly with medication, surgery is usually necessary to prevent colon rupture.

Crohn's disease can occur in all regions of the gastrointestinal tract. With this disease intestinal obstruction due to inflammation and fibrosis occurs in a large number of patients. Granulomas and fistula formation are frequent complications of Crohn's disease. Disease progression consequences include intravenous feeding, surgery and colostomy.

The most commonly used medications to treat IBD are anti-inflammatory drugs such as the salicylates. The salicylate preparations have been effective in treating mild to moderate disease. They can also decrease the frequency of disease flares when the medications are taken on a prolonged basis. Examples of salicylates include sulfasalazine, olsalazine, and mesalamine. All of these medications are given orally in high doses for maximal therapeutic benefit. These medicines are not without side effects. Azulfidine can cause upset stomach when taken in high doses, and rare cases of mild kidney inflammation have been reported with some salicylate preparations.

Corticosteroids are more potent and faster-acting than salicylates in the treatment of IBD, but potentially serious side effects limit the use of corticosteroids to patients with more severe disease. Side effects of corticosteroids usually occur with long term use. They include thinning of the bone and skin, infections, diabetes, muscle wasting, rounding of faces, psychiatric disturbances, and, on rare occasions, destruction of hip joints.

In IBD patients that do not respond to salicylates or corticosteroids, medications that suppress the immune system are used. Examples of immunosuppressants include azathioprine and 6-mercaptopurine. Immunosuppressants used in this situation help to control IBD and allow gradual reduction or elimination of corticosteroids. However, immunosuppressants cause increased risk of infection, renal insufficiency, and the need for hospitalization.

Clearly there is a great need for agents capable of preventing and treating IBD. It would be desirable if such agents could be administered in a cost-effective and timely fashion, with a minimum of adverse side effects.

SUMMARY OF THE INVENTION

The present invention relates to therapeutics for the prevention and treatment of vitamin D responsive diseases in humans, as well as other animals, through the use of biologically active vitamin D compounds in combination with at least one other immunomodulatory compound such as interleukin-10, interleukin-4, or TNFα inhibitor. The present invention also relates to therapeutics for the prevention and treatment of IBD. Specifically, the present invention contemplates the prevention and treatment of IBD in humans as well as other animals through the use of biologically active vitamin D compounds.

The present invention provides methods of treatment, comprising; providing a subject and a therapeutic composition comprising a biologically active vitamin D compound; and administering the therapeutic composition to the subject. It is not intended that the present invention be limited to any particular subject. Indeed, a variety of subjects are contemplated. In some embodiments, the subject is a mammal. In a further embodiment, the subject is a mammal selected from the group of a human, horse, non-human primate, dog, and cat. In some embodiments, the subject is a bird (e.g. chicken, turkey, duck, pigeon, ostrich, etc.). In a preferred embodiment, the subject is a human. In an additional embodiment, the subject is on a low calcium diet. In some embodiments, the subject is screened for IL-10 production prior to the administration of the composition comprising a biologically active vitamin D compound. In other embodiments, the subject is IL-10 deficient and the therapeutic composition administered to the subject comprises a biologically active vitamin D compound and IL-10. In certain embodiments, the subject is not IL-10 deficient and the therapeutic composition administered to the subjected comprises a biologically active vitamin D compound and IL-10.

In particular embodiments, the subject is suffering from symptoms of inflammatory bowel disease. In another embodiment, the subject is suffering from ulcerative colitis. In a different embodiment, the subject is suffering from Crohn's disease. In a preferred embodiment, the administration of a therapeutic composition comprising a biologically active vitamin D compound reduces the symptoms of disease (i.e. reduces the symptoms of inflammatory bowel disease, ulcerative colitis, or Crohn's disease). In another embodiment, the biologically active vitamin D compounds are administered under conditions such that the symptoms of IBD are reduced. In a different embodiment, the subject is at risk for inflammatory bowel disease, and the therapeutic composition is administered prophylactically. In still further embodiments, a therapeutically effective amount of a biologically active vitamin D compound is administered to the subject.

It is not intended that the present invention be limited to particular biologically active vitamin D compounds. A variety of biologically active vitamin D compounds are contemplated. In other embodiments, the biologically active vitamin D compound is selected from vitamin D, 1,25 dihydroxyvitamin $D_3$, 1α-hydroxyvitamin $D_3$, 1,25-dihydroxyvitamin $D_2$, 1α-hydroxyvitamin $D_2$, 1α,25-$(OH)_2$-16-ene-$D_3$, 1α,25-$(OH)_2$-24-oxo-16-ene-$D_3$, 1α,24R $(OH)_2$-$D_3$, 1α,25$(OH)_2$-22-oxa-$D_3$, 20-epi-22-oxa-24a, 24b,-dihomo-1α,25$(OH)_2$-$D_3$, 20-epi-22-oxa-24a,26a,27a,-trihomo-1α,25$(OH)_2$-$D_3$, 20-epi-22-oxa-24homo-1α,25 $(OH)_2$-$D_3$, 1,25-$(OH)_2$-16,23E-diene-26-trifluoro-19-nor-$D_3$. In a preferred embodiment, the biologically active vitamin D compound is selected from 1,25-dihydroxyvitamin $D_3$, 19-nor-1,25-dihydroxyvitamin $D_2$, 19-nor-1,25-dihydroxy-21-epi-vitamin $D_3$, 1,25-dihydroxy-24-homo-22-dehydro-22E-vitamin $D_3$, and 19-nor-1,25-dihydroxy-24-homo-22-dehydro-22E-vitamin $D_3$, and non-secosteroidal vitamin D mimics. In a particularly preferred embodiment, the biologically active compound is 1α-hydroxyvitamin $D_3$. In an additional embodiment, the biologically active vitamin D compound is selected from the analogs represented by the following formula:

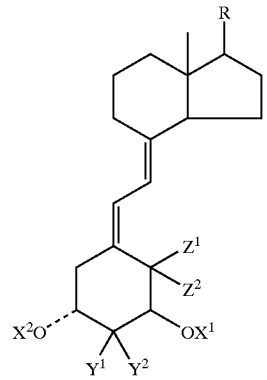

wherein $X^1$ and $X^2$ are each selected from the group consisting of hydrogen and acyl;

wherein $Y^1$ and $Y^2$ can be H, or one can be O-aryl or O-alkyl while the other is hydrogen and can have a β or α configuration; $Z^1$ and $Z^2$ are both H, or $Z^1$ and $Z^2$ taken together are $CH_2$; and wherein R is an alkyl, hydroxyalkyl or fluoroalkyl group, or R may represent the following side chain:

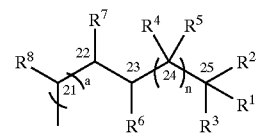

wherein (a) may have an S or R configuration and wherein $R^1$ represents hydrogen, hydroxy or O-acyl, $R^2$ and $R^3$ are each selected from the group consisting of alkyl, hydroxyalkyl and fluoroalkyl, or, when taken together represent the group—$(CH_2)_m$—where m is an integer having a value of from 2 to 5, $R^4$ is selected from the group consisting of hydrogen, hydroxy, fluorine, O-acyl, alkyl, hydroxyalkyl and fluoroalkyl, $R^5$ is selected from the group consisting of hydrogen, hydroxy, fluorine, alkyl, hydroxyalkyl and fluoroalkyl, or, $R^4$ and $R^5$ taken together represent double-bonded oxygen, $R^6$ and $R^7$ taken together form a carbon—carbon double bond and $R^8$ may be H or $CH_3$, and wherein n is an integer having a value of from 1 to 5, and wherein the carbon at any one of positions 20, 22, or 23 in the side chain may be replaced by an O, S, or N atom.

In certain embodiments, the biologically active vitamin D compounds of the present invention do not cause symptoms of hypercalcemia when administered to a subject. In another preferred embodiment of the present invention, the biologically active vitamin D compounds of the present invention do not generate as much (i.e. a lesser degree) of a calcemic response as compared to calcitriol when administered to a subject. In some embodiments, the biologically active vitamin D compounds have low calcemic response characteristics, inhibit cell proliferation and promote cell differentiation as compared to calcitriol. In another embodiment, these compounds are selected from 1α,25-$(OH)_2$-24-epi-$D_2$, 1α,25-$(OH)_2$-24a-Homo-$D_3$, 1α,25-$(OH)_2$-24a-Dihomo-$D_3$, 1α,25-$(OH)_2$-19-nor-$D_3$, and 20-epi-24-homo-1α,25-$(OH)_2$-$D_3$.

The present invention also contemplates the administration of a therapeutic composition comprising more than one of the biologically active compounds of the present invention. In other embodiments, the biologically active compounds of the present invention are administered in therapeutically effective amounts. In certain embodiments, a preferred dose of the biologically active vitamin D compound for the present invention is the maximum that a patient can tolerate and not develop serious hypercalcemia. In another embodiment, if the biologically active vitamin D compound is not a 1α-hydroxy compound, a daily dose between 1.0 and 100 μg per day per 160 pound patient is administered, while a particularly advantageous daily dose is between 5.0 and 50 μg per day per 160 pound patient. In a different embodiment, if the biologically active vitamin D compound is a 1α-hydroxy compound, a daily dose of between 0.1 and 20 μg per day per 160 pound patient is administered, while a preferred dose is between 0.5 and 10 μg per day per 160 pound patient. In a particularly preferred embodiment, the dose is between 3–10 μg per day. In an additional embodiment, the therapeutic administration of the biologically active vitamin D compounds does not cause serious hypercalcemia. In another embodiment, the therapeutic administration of the biologically active vitamin D compounds only causes mild hypercalcemia. In another embodiment, the biologically active vitamin D compounds do not cause symptoms of hypercalcemia.

It is not intended that the present invention be limited to a particular mode of administration. A variety of modes of administration are contemplated, including intravenously, intramuscularly, subcutaneously, intradermally, intraperitoneally, intrapleurally, intrathecally, orally, rectally and topically. In certain embodiments, the therapeutic compositions are administered via suppository, or in tablet or capsule formulations for oral delivery. In other embodiments, administration of the therapeutic compositions occurs at night. In another embodiment, multiple doses (e.g. 3 or 4) are provided in a 24 hour period. In a further embodiment, the administration of the therapeutic composition is by pulse intravenous therapy. In a particularly preferred embodiment, the therapeutic compositions are administered via a transdermal patch (skin patch).

The present invention also provides methods of treatment, comprising, providing a subject with symptoms of inflammatory bowel disease and a therapeutic composition comprising a biologically active vitamin D compound, and administering the therapeutic compound to the subject. In some embodiments, the biologically active vitamin D compounds are administered to a patient after the surgical removal of damaged tissue. In a preferred embodiment, the present invention provides a method of treatment, comprising, providing a human patient with symptoms of inflammatory bowel disease, a therapeutic composition comprising a biologically active vitamin D compound, and administering the therapeutic composition to the patient under conditions such that the symptoms are reduced. In some embodiments, the subject is screened for the presence of interleukin-10 prior to the administration of the composition comprising a biologically active vitamin D compound. In other embodiments, the subject is a male. In certain embodiments, the subject is administered IL-10 in addition to a biologically active vitamin D compound. In some embodiments, the subject is an IL-10 deficient subject.

The present invention also provides methods of treatment, comprising, providing a subject at risk for inflammatory bowel disease and a therapeutic composition comprising a biologically active vitamin D compound, and prophylactically administering the therapeutic compound to the subject. In a preferred embodiment, the prophylactic administration of the biologically active vitamin D compounds delays the onset of the symptoms of inflammatory bowel disease. In a particularly preferred embodiment, the prophylactic administration of the biologically active vitamin D compounds prevents the onset of one or more symptoms of inflammatory bowel disease (e.g. prevents the onset of abdominal pain, diarrhea, rectal bleeding, weight loss, fever, loss of appetite, dehydration, anemia, or malnutrition, or any combination thereof). In some embodiments, the subject is screened for the presence of interleukin-10 prior to the administration of the composition comprising a biologically active vitamin D compound. In certain embodiments, the subject is administered both a biologically active vitamin D compound and IL-10. In some embodiments, the subject is an IL-10 deficient subject and is administered both IL-10 and a biologically active vitamin D compound.

The present invention also provides a composition of matter comprising a transdermal patch, wherein the transdermal patch comprises a therapeutic composition comprising biologically active vitamin D compounds. In some embodiments, the transdermal patch comprises a therapeutically effective amount of a biologically active vitamin D compound. In certain embodiments, the transdermal patch further comprises IL-10. In certain embodiments, the IL-10 is administered via an route such as subcutaneous, or intravenous (e.g. injection of IL-10 protein, virus-mediated gene transfer of the IL-10 gene, injection of DNA comprising the IL-10 gene, and liposomes encasing the IL-10 protein). In another embodiment, the transdermal patch further comprises a single polymer. In an additional embodiment, the transdermal patch further comprises multiple polymers. In another embodiment, the transdermal patch further comprises a polyurethane acrylic copolymer. In another embodiment, the transdermal patch further comprises silicone or polyisobutylene or both. In a preferred embodiment, the transdermal patch is worn by a subject at risk for Inflammatory Bowel Disease. In another preferred embodiment, the transdermal patch is worn by a subject with symptoms of Inflammatory Bowel Disease. In another embodiment, the transdermal patch delivers biologically active vitamin D compounds to a subject in a continuous manner under conditions such that symptoms of IBD are reduced.

The present invention also provides a method of treatment, comprising, providing an IL-10 deficient subject with symptoms of inflammatory bowel disease and a therapeutic composition comprising a biologically active vitamin D compound and IL-10, and administering the therapeutic compound to the subject. The present invention also provides a method of treatment, comprising, providing an IL-10 deficient subject at risk for inflammatory bowel disease and a therapeutic composition comprising a biologically active vitamin D compound and IL-10, and prophylactically administering the therapeutic compound to the subject.

In some embodiments, the present invention provides therapeutic compositions comprising a biologically active vitamin D compound and IL-10 (e.g. a therapeutic amount of a biologically active vitamin D compound and a therapeutic amount of IL-10). In other embodiments, the present invention provides a transdermal patch comprising a biologically active vitamin D compound and IL-10 (or the IL-10 is administered some alternate route). In some embodiments, the present invention provides a suppository comprising a biologically active vitamin D compound and IL-10. In still other embodiments, the present invention provides kits comprising a biologically active vitamin D compound, and IL-10 (e.g. in separate containers, or separate pills or as part of separate devices). In some embodiment, the kit further comprises instructions for employing the biologically active vitamin D compound and IL-10 to treat or prevent disease (e.g. a printed insert describing the use of these compounds). In preferred embodiments, the instructions describe the treatment of IBD with a biologically active vitamin D compound and IL-10.

In some embodiments, the present invention provides methods for treatment, comprising: a) providing: i) a subject with symptoms of at least one vitamin D responsive disease, ii) a biologically active vitamin D compound, and iii) interleukin-10; and b) administering a therapeutically effective amount of the biologically active vitamin D compound, and a therapeutically effective amount of the interleukin-10, to the subject under conditions such that the symptoms are reduced. In certain embodiments, the biologically active vitamin D compound and the interleukin-10 are part of a single therapeutic composition (e.g. such that the administration may be accomplished with a single composition). In other embodiments, the biologically active vitamin D compound and interleukin-10 are separate compositions (e.g. such that each composition may be administered separately to the subject). In preferred embodiments, the biologically active vitamin D compound and the interleukin-10 are administered to the subject at about the same time (e.g., within a few seconds, minutes, or hours of each other).

In particular embodiments, the present invention provides methods for treatment, comprising: a) providing: i) a subject with symptoms of at least one vitamin D responsive disease, ii) a biologically active vitamin D compound, and iii) interleukin-4; and b) administering a therapeutically effective amount of the biologically active vitamin D compound, and a therapeutically effective amount of the interleukin-4, to the subject under conditions such that the symptoms are reduced. In certain embodiments, the biologically active vitamin D compound and the interleukin-4 are part of a single therapeutic composition (e.g. such that the administration may be accomplished with a single composition). In other embodiments, the biologically active vitamin D compound and interleukin-4 are separate compositions (e.g. such that each composition may be administered separately to the subject). In preferred embodiments, the biologically active vitamin D compound and the interleukin-4 are administered to the subject at about the same time (e.g., within a few seconds, minutes, or hours of each other). In certain embodiments, administration is in the form of an intranasal spray (e.g. comprising a biologically active compound and/or IL-10).

In other embodiments, the present invention provides methods for treatment, comprising: a) providing: i) a subject with symptoms of at least one vitamin D responsive disease, ii) a biologically active vitamin D compound, and iii) a TNFα inhibitor (e.g. anti-TNFα antibody); and b) administering a therapeutically effective amount of the biologically active vitamin D compound, and a therapeutically effective amount of the TNFα inhibitor, to the subject under conditions such that the symptoms are reduced. In certain embodiments, the biologically active vitamin D compound and the TNFα inhibitor are part of a single therapeutic composition (e.g. such that the administration may be accomplished with a single composition). In other embodiments, the biologically active vitamin D compound and TNFα inhibitor are separate compositions (e.g. such that each composition may be administered separately to the subject). In preferred embodiments, the biologically active vitamin D compound and the TNFα inhibitor are administered to the subject at about the same time (e.g., within a few seconds, minutes, or hours of each other).

In some embodiments, the present invention provides methods of treatment, comprising; a) providing: i) a subject with symptoms of at least one vitamin D responsive disease, and ii) a therapeutic composition comprising a biologically active vitamin D compound and interleukin-10; and b) administering a therapeutically effective amount of the therapeutic composition to the subject under conditions such that the symptoms are reduced. In other embodiments, the present invention provides methods of treatment comprising; a) providing: i) a subject with symptoms of at least one vitamin D responsive disease, and ii) a therapeutic composition comprising a biologically active vitamin D compound and interleukin-4; and b) administering a therapeutically effective amount of the therapeutic composition to the subject under conditions such that the symptoms are reduced. In certain embodiments, the present invention provides methods of treatment, comprising: a) providing: i) a subject with symptoms of at least one vitamin D responsive disease, and ii) a therapeutic composition comprising a biologically active vitamin D compound and a TNFα inhibitor; and b) administering a therapeutically effective amount of the therapeutic composition to the subject under conditions such that the symptoms are reduced.

In certain embodiments, the present invention provides methods of treatment comprising; a) providing; i) a subject at risk for at least one vitamin D responsive disease, ii) a biologically active vitamin D compound, and iii) interleukin-10; and b) prophylactically administering the biologically active vitamin D compound and the interleukin-10 to the subject. In some embodiments, the present invention provides methods of treatment comprising; a) providing; i) a subject at risk for at least one vitamin D responsive disease, ii) a biologically active vitamin D compound, and iii) interleukin-4; and b) prophylactically administering the biologically active vitamin D compound and the interleukin-4 to the subject. In particular embodiments, the present invention provides methods of treatment comprising; a) providing; i) a subject at risk for at least one vitamin D responsive disease, ii) a biologically active vitamin D compound, and iii) a TNFα inhibitor; and b) prophylactically administering the biologically active vitamin D compound and the TNFα inhibitor to the subject.

In certain embodiments, the present invention provides methods of treatment, comprising; a) providing: i) a subject at risk for at least one vitamin D responsive disease, and ii) a therapeutic composition comprising a biologically active vitamin D compound and interleukin-10; and b) prophylactically administering the therapeutic composition to the subject. In some embodiments, the present invention provides methods of treatment, comprising; a) providing: i) a subject at risk for at least one vitamin D responsive disease, and ii) a therapeutic composition comprising a biologically active vitamin D compound and interleukin-4; and b) prophylactically administering the therapeutic composition to the subject. In additional embodiments, the present invention provides methods of treatment, comprising; a) providing: i) a subject at risk for at least one vitamin D responsive disease, and ii) a therapeutic composition comprising a biologically active vitamin D compound and a TNFα inhibitor; and b) prophylactically administering the therapeutic composition to the subject. In particular embodiments, the administration delays the onset of symptoms of the at least one vitamin D responsive disease. In preferred embodiments, the subject at risk for the at least one vitamin D responsive disease is a human.

In some embodiments of the present invention, the administration step does not cause serious hypercalcemia. In other embodiments, the administration step does not cause symptoms of hypercalcemia. In certain embodiments, the methods of the present invention further comprise determining if the subject is an IL-10 deficient subject. In particular embodiments, the at least one vitamin D responsive disease is selected from the group consisting of osteoporosis, renal osteodystrophy, psoriasis, multiple sclerosis, arthritis, ulcerative colitis, and Crohn's disease. In preferred embodiments, the at least one vitamin D responsive disease is ulcerative colitis or Crohn's disease. In other preferred embodiments, the administering is via a transdermal patch.

In certain embodiments, the therapeutically effective amount comprises a daily dose for the biologically active vitamin D compound of at least 5 µg per day (e.g., at least 5 µg, at least 8 µg, at least 10 µg, at least 15 µg, at least 20 µg and at least 25 µg per day). In some embodiments, the therapeutically effective amount comprises a daily dose for the biologically active vitamin D compound of between 0.1 µg and 20 µg; 0.5 µg and 10 µg; and 3.0 µg and 10 µg. In particular embodiments, the daily dose of the biologically active vitamin D compound is greater than the maximum the subject can tolerate without developing serious hypercalcemia when the biologically active vitamin D compound is administered without interleukin-10 (e.g. the IL-10 allows the patient to receive more biologically active vitamin D compound than would be possible if no IL-10 were administered).

In certain embodiments, the therapeutically effective amount comprises a daily dose for the interleukin-10 of approximately 5 µg per kilogram (of subject) per day. In certain embodiments, the therapeutically effective amount comprises a daily dose for the interleukin-10, per kilogram of subject, of approximately 2 µg, 3 µg, 4 µg, 5 µg, 6 µg, 7 µg, 8 µg, 10 µg, 12 µg, 14, or 20 µg. In particular embodiments, the therapeutically effective amount comprises a daily dose for the interleukin-10, per kilogram of subject, of between 1 µg and 20 µg; 3 µg and 10 µg; and 4 µg and 6 µg.

In some embodiments, the therapeutically effective amount comprises a daily dose for the interleukin-4 of approximately 5 µg per kilogram (of subject) per day. In certain embodiments, the therapeutically effective amount comprises a daily dose for the interleukin-4, per kilogram of subject, of approximately 2 µg, 3 µg, 4 µg, 5 µg, 6 µg, 7 µg, 8 µg, 10 µg, 12 µg, 14, or 20 µg. In particular embodiments, the therapeutically effective amount comprises a daily dose for the interleukin-4, per kilogram of subject, of between 1 µg and 20 µg; 3 µg and 10 µg; and 4 µg and 6 µg.

In particular embodiments, the therapeutically effective amount comprises a weekly or bi-weekly dose for a TNFα inhibitor (e.g. anti-TNFα antibody) of approximately 20 mg per kilogram (of subject), or 40 mg per kilogram, or 60 mg per kilogram. In certain embodiments, the therapeutically effective amount comprises a weekly or bi-weekly dose for a TNFα inhibitor (e.g. anti-TNFα antibody), per kilogram of subject, of approximately 10–70 mg, 20–50, or 30–40 mg. In particular embodiments, the therapeutically effective amount comprises a one time dose of a TNFα inhibitor (e.g. anti-TNFα antibody) of 3–10 mg per kilogram of subject (e.g. approximately 5 mg per kilogram of subject). In other embodiments, the therapeutically effective amount comprises a daily dose of a TNFα inhibitor (e.g., anti-TNFα antibody) of approximately 1–2 mg or 5, 10, or 20 mg per kilogram of subject.

In some embodiments, the present invention provides compositions comprising a therapeutically effective amount of a biologically active vitamin D compound, and a therapeutically effective amount of interleukin-10. In certain embodiments, the compositions comprise a first amount of a biologically active vitamin D compound, and a second amount of interleukin-10, wherein the first amount is between 0.01 µg and 50 µg, and wherein the second amount is between 25 µg and 500 µg. In some embodiments, the second amount is between 175 µg–400 µg. In other embodiments, the second amount is between 250 µg–350 µg (e.g., approximately 75 µg, approximately 150 µg, approximately 225 µg, or approximately 300 µg).

In other embodiments, the present invention provides compositions comprising a therapeutically effective amount of a biologically active vitamin D compound, and a therapeutically effective amount of interleukin-4. In some embodiments, the present invention provides compositions comprising a first amount of a biologically active vitamin D compound, and a second amount of interleukin-4, wherein the first amount is between 0.01 µg and 50 µg, and wherein the second amount is between 25 µg and 500 µg. In some embodiments, the second amount is between 175 µg–400 µg. In other embodiments, the second amount is between 250 µg–350 µg (e.g., approximately 75 µg, approximately 150 µg, approximately 225 µg, or approximately 300 µg).

In yet other embodiments, the present invention provides compositions comprising a therapeutically effective amount of a biologically active vitamin D compound, and a therapeutically effective amount of a TNFα inhibitor (e.g. anti-TNFα antibody). In certain embodiments, the compositions comprise a first amount of a biologically active vitamin D compound, and a second amount of an anti-TNFα antibody, wherein the first amount is between 0.01 µg and 50 µg, and wherein the second amount is between 1 mg and 5 mg. In some embodiments, the anti-TNFα antibody comprises Human Anti-TNF Antibody D2E7 (Abbot Laboratories). In other embodiments, the anti-TNF antibody comprises CDP571. In preferred embodiments, the anti-TNFα antibody comprises REMICADE (infliximab).

In certain embodiments, the present invention provides compositions comprising a biologically active vitamin D compound, interleukin-10, and/or interleukin-4, and/or a TNFα inhibitor (e.g. anti-TNFα antibody). In particular embodiments, the interleukin-10, interleukin-4, and TNFα inhibitor are human, or derived from a human source. In some embodiments, the anti-TNFα antibody is humanized. In particular embodiments, the interleukin-10, interleukin-4, and TNFα inhibitor (e.g. anti-TNFα antibody) are recombinant. In preferred embodiments, the biologically active vitamin D compound is 1,25-dihydroxyvitamin $D_3$ (i.e. calcitriol). In other preferred embodiments, the biologically active vitamin D compound is 1α-hydroxyvitamin $D_3$ (i.e. alphacalcidol).

In some embodiments, the present invention provides devices comprising a transdermal patch, wherein the transdermal patch comprises a biologically active vitamin D compound and interleukin-10. In other embodiments, the transdermal patch comprises a therapeutically effective amount of a biologically active vitamin D compound, and a therapeutically effective amount of interleukin-10. In further embodiments, the transdermal patch comprises a first amount of a biologically active vitamin D compound, and a second amount of interleukin-10, wherein the first amount is between 0.01 µg and 50 µg, and wherein the second amount is between 25 µg and 500 µg.

In other embodiments, the present invention provides devices comprising a transdermal patch, wherein the transdermal patch comprises a biologically active vitamin D compound and interleukin-4. In other embodiments, the transdermal patch comprises a therapeutically effective amount of a biologically active vitamin D compound, and a therapeutically effective amount of interleukin-4. In further embodiments, the transdermal patch comprises a first amount of a biologically active vitamin D compound, and a second amount of interleukin-4, wherein the first amount is between 0.01 µg and 50 µg, and wherein the second amount is between 25 µg and 500 µg.

In further embodiments, the present invention provides devices comprising a transdermal patch, wherein the transdermal patch comprises a biologically active vitamin D compound and anti-TNFα antibody. In particular embodiments, the transdermal patch comprises a therapeutically effective amount of a biologically active vitamin D compound, and a therapeutically effective amount of anti-TNFα antibody. In certain embodiments, the transdermal patch comprises a first amount of a biologically active vitamin D compound, and a second amount of anti-TNFα antibody, wherein the first amount is between 0.01 µg and 50 µg, and wherein the second amount is between 1 mg and 30 mg.

In some embodiments, the present invention provides kits and systems comprising at least one biologically active vitamin D compound and interleukin-10. In particular embodiments, the kits and systems comprise a first amount of a biologically active vitamin D compound, and a second amount of interleukin-10, wherein the first amount is between 0.01 µg and 50 µg, and wherein the second amount is between 25 µg and 500 µg. In some embodiments, the biologically active vitamin D compound is in tablet form, and the interleukin-10 is in injectable form (e.g. liquid form). In certain embodiments, the kits further comprise a syringe. In particular embodiments, both the biologically active vitamin D compound and interleukin-10 are in injectable form, or both of these components are in tablet form. In other embodiments, the kits and systems of the present invention comprise an insert component (e.g. written instructions for treating at least one vitamin D responsive disease).

In certain embodiments, the present invention provides kits and systems comprising at least one biologically active vitamin D compound and interleukin-4. In particular embodiments, the kits and systems comprise a first amount of a biologically active vitamin D compound, and a second amount of interleukin-4, wherein the first amount is between 0.01 µg and 50 µg, and wherein the second amount is between 25 µg and 500 µg. In other embodiments, the kits and systems of the present invention comprise an insert component (e.g. written instructions for treating at least one vitamin D responsive disease).

In further embodiments, the present invention provides kits and systems comprising at least one biologically active vitamin D compound and anti-TNFα antibody. In particular embodiments, the kits and systems comprise a first amount of a biologically active vitamin D compound, and a second amount of anti-TNFα antibody, wherein the first amount is between 0.01 µg and 50 µg, and wherein the second amount is between 1 mg and 40 mg. In other embodiments, the kits and systems of the present invention comprise an insert component (e.g. written instructions for treating at least one vitamin D responsive disease).

In other embodiments, the present invention provides methods for screening compounds for hypercalcemic potential, comprising; a) providing; i) an interleukin-10 deficient subject; and ii) a biologically active vitamin D compound, and b) administering the biologically active vitamin D compound to the interleukin-10 deficient subject, and c) measuring the calcemic response of the interleukin-10 deficient subject to the biologically active vitamin D compound. In some embodiments, the present invention provides methods for screening compounds for hypercalcemic potential, comprising; a) providing; i) an interleukin-10 deficient subject; and ii) a biologically active vitamin D compound, and b) administering the biologically active vitamin D compound to the interleukin-10 deficient subject, and c) determining if the biologically active vitamin D compound causes symptoms of hypercalcemia in the interleukin-10 deficient subject. In preferred embodiments, the interleukin-10 deficient subject is a mouse or a rat.

Definitions

The phrase "vitamin D compounds" include, but are not limited to compounds which have at least one of the following features: the C-ring, D-ring and 3β-hydroxycyclohexane A-ring of vitamin D interconnected by the 5,7 diene double bond system of vitamin D together with any side chain attached to the D-ring (i.e. compounds with a 'vitamin D nucleus' and substituted or unsubstituted A-, C-, and D-rings interconnected by a 5,7 diene double bond system typical of vitamin D together with a side chain attached to the D-ring).

The phrase "nonsecosteroidal vitamin D mimics" is defined as nonsecosteroid compounds which are capable of mimicking various activities of the secosteroid calcitriol. Examples of such compounds include, but are not limited to, LG190090, LG190119, LG190155, LG190176, and LG1900178 [See, Boehm et al., *Chemistry & Biology* 6:265–275 (1999)].

The phrase "biologically active vitamin D compound" is defined as encompassing vitamin D compounds and non-secosteroidal vitamin D mimics which are biologically active in vivo, or are acted upon in a subject (i.e. host) such that the compound becomes active in vivo. Examples of such compounds include, but are not limited to: vitamin D, 1,25 dihydroxyvitamin $D_3$ (1,25$(OH)_2D_3$) [a.k.a. calcitriol], and analogs thereof [e.g. 1α-hydroxyvitamin $D_3$ (1α-OH-$D_3$), 1,25-dihydroxyvitamin $D_2$ (1,25-$(OH)_2D_2$), 1α-hydroxyvitamin $D_2$ (1α-OH-$D_2$), 1α,25-$(OH)_2$-16-ene-$D_3$, 1α,25-$(OH)_2$-24-oxo-16-ene-$D_3$, 1α,24R$(OH)_2$-$D_3$, 1α,25$(OH)_2$-22-oxa-$D_3$, 20-epi-22-oxa-24a,24b,-dihomo-1α,25$(OH)_2$-$D_3$, 20-epi-22-oxa-24a,26a,27a,-trihomo-1α,25$(OH)_2$-$D_3$, 20-epi-22-oxa-24homo-1α,25$(OH)_2$-$D_3$, 1,25-$(OH)_2$-16,23E-diene-26-trifluoro-19-nor-$D_3$, and nonsecosteroidal vitamin D mimics. Further examples are provided below, including various structural formulas, detailed in part III.

The phrase "symptoms of IBD" is herein defined to include symptoms, including, but not limited to, abdominal pain, diarrhea, rectal bleeding, weight loss, fever, loss of appetite, and other more serious complications, such as dehydration, anemia and malnutrition. A number of such symptoms are subject to quantitative analysis (e.g. weight loss, fever, anemia, etc.). Some symptoms are readily determined from a blood test (e.g. anemia) or a test that detects the presence of blood (e.g. rectal bleeding).

The phrase "calcemic response" is herein defined as the biological response related to alterations in calcium metabolism that are caused by many biologically active vitamin D compounds (e.g. calcitriol) when administered to a subject. The response includes, but is not limited to, elevated calcium concentrations in serum, increased intestinal absorption of dietary calcium, increased urinary calcium excretion, and increased bone calcium mobilization.

The phrase "symptoms of hypercalcemia" is herein defined to be detected symptoms including, but not limited to, a serum calcium concentration that is above the normal range of 8.5 to 10.5 mg/dL, central nervous system (CNS) signs like muscle weakness, lethargy, and coma, gastrointestinal signs like constipation, anorexia, nausea, and vomiting, cardiovascular signs like shortening of the QT interval, hypotension, and arrhythmias, and renal signs like nephrocalcinosis, nephrolithiasis, and uremia (See, Chan et al., 1997, Current Problems in Surgery, 34:445–523; and Jan de Deur et al., 1997, Current Therapy in Endocrinology & Metabolism, 6:551–556, both of which are herein incorporated by reference).

The phrase "mild hypercalcemia" is herein defined as the condition where a subject has a serum calcium concentration that is above the normal range, but less than 12.0 mg/dL. This asymptomatic condition occurs in about 5% of the population (See, e.g., Jan de Beur, Supra). This condition is generally not life threatening and does not require immediate medical attention and intervention.

The phrase "moderate hypercalcemia" is herein defined as the condition where a subject has a serum calcium concentration exceeding 12.0 mg/dL, and may also be suffering from some other signs of hypercalcemia. Examples include, but are not limited to, apathy, drowsiness, confusion, lethargy, constipation, hypotension, nephrocalcinosis, and nephrolithiasis (See, e.g. Jan de Beur, Supra). Moderate hypercalcemia generally requires careful clinical evaluation to determine the type and urgency of medical intervention to prevent life threatening illness or death.

The phrase "severe hypercalcemia" is herein defined as the condition where a subject has a serum calcium concentration exceeding 14.0 mg/dL, and is also suffering from some other signs of hypercalcemia. Examples include, but are not limited to, muscle weakness, lethargy or coma, nausea, and vomiting, and shortening of the QT interval and arrhythmia. Severe hypercalcemia is a life threatening condition that generally requires immediate and vigorous medical intervention to prevent death.

The phrase "a therapeutically effective amount" of a biologically active vitamin D compound is herein defined as the dosage level required for a patient such that the symptoms of IBD, or any other vitamin D responsive disease, are reduced.

The phrase "a therapeutically effective amount" of IL-10 or a TNFα inhibitor is herein defined as the dosage level required for a patient such that the symptoms of IBD, or the symptoms of any other IL-10-responsive or TNFα inhibitor responsive disease, are reduced.

The phrase "under conditions such that the symptoms are reduced" refers to any degree of qualitative or quantitative reduction in detectable symptoms of IBD or any other vitamin D responsive disease, including but not limited to, a detectable impact on the rate of recovery from disease (e.g. rate of weight gain), or the reduction of at least one of the following symptoms: abdominal pain, diarrhea, rectal bleeding, weight loss, fever, loss of appetite, dehydration, anemia, distention, fibrosis, inflamed intestines and malnutrition.

The phrase "at risk for IBD" is herein defined as encompassing the segment of the world population that has an increased risk (i.e. over the average person) for IBD. IBD is most commonly found in young adults, but can occur at any age. It occurs worldwide, but is most common in the United States, England, and northern Europe. It is especially common in people of Jewish descent. An increased frequency of this condition has been recently observed in developing nations. Increased risk is also present in people with biological first degree relatives who suffer from inflammatory bowel disease.

The phrase "therapeutic composition comprising biologically active vitamin D compounds" refers to compositions containing the biologically active vitamin D compounds of the present invention, or the biologically active vitamin D compounds of the present invention provided together with one or more other compounds or agents including, but not limited to, other biologically active vitamin D compounds, IL-10, IL-4, IL-15, TNFα inhibitor, physiologically tolerable liquids, gels, carriers, diluents, adjuvants, excipients, salicylates, steroids, immunosuppressants, antibodies, cytokines, antibiotics, binders, fillers, preservatives, stabilizing agents, emulsifiers, and buffers.

The phrase "continuous manner" when used in reference to the method of delivery or administration of the biologically active vitamin D compounds of the present invention, is defined as meaning a substantially uninterrupted administration of the compounds of the present invention, such that a therapeutic dosage is stretched over a period of time and avoids a dosage 'spike' of high blood concentration followed by nadir of low blood concentration with each dosing which is common among other modes of administration (e.g. injection). Examples of modes of administration which employ a continuous manner of delivery include, but are not limited to, a transdermal patch, a suppository, a pro-drug or a slow release oral formulation.

The word "subject" refers to a patient which is administered the therapeutic composition comprising biologically active vitamin D compounds of the present invention. Examples of subjects, include, but are not limited to, humans and other animals such as non-human primates, birds, horses, dogs, and cats.

The word "IL-10 deficient subject" refers to a patient or test animal that is known (or determined) to produce less IL-10 (interleukin-10) than a wild-type subject. Examples include, but are not limited to, subjects that produce 90%, 50%, or 10% of wild-type levels of IL-10, or subjects that do not produce any IL-10. The term IL-10 deficient subject also refers to a patient that is known (or determined) to have an abnormally low response to IL-10 as compared to the wild-type response to IL-10.

The term "vitamin D responsive disease" refers to any disease that is shown to be treatable, at least in part, with biologically active vitamin D compounds. Examples of vitamin D responsive diseases include, but are not limited to, osteoporosis, renal osteodystrophy, psoriasis, multiple sclerosis, arthritis, ulcerative colitis, and Crohn's disease. The term "symptoms of at least one vitamin D responsive disease refers to those symptoms generally associated with a particular disease.

The term "tumor necrosis factor alpha inhibitors" or "TNFα inhibitors" refer to molecules that are able to bind to TNFα. Example of TNFα inhibitors include, but are not limited to, antagonists described in U.S. Pat. No. 5,795,967 to Aggarwal, and polyclonal, monoclonal, humanized, and chimeric antibodies to TNFα or the TNFα receptor (e.g. described in U.S. Pat. No. 6,277,969 to Le et al.; U.S. Pat. No. 5,654,407 to Boyle et al.; U.S. Pat. Nos. 6,090,382 and 6,258,562 assigned to BASF; U.S. Pat. No. 6,090,923 to Wallach et al.; U.S. Pat. No. 6,270,766 to Feldmann et al.; and U.S. Pat. Nos. 5,644,034 and 5,959,087, all of which are herein incorporated by reference). Particular TNFα inhibitors include, but are not limited to, INFLIXIMAB, CDP571, D2E7, TNFα receptor fusion proteins such as ETANERCEPT, thalidomide and thalidomide analogous that inhibit TNFα production (See, Sandborn, 2001, Inflamm. Bowel. Dis., 7 Suppl, 1:S9–16, herein incorporated by reference).

DESCRIPTION OF THE INVENTION

Figure 1:
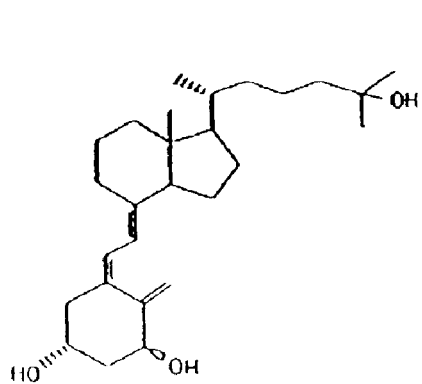
FIG. 1 depicts six biologically active vitamin D compounds useful in the present invention.
Figure 1:
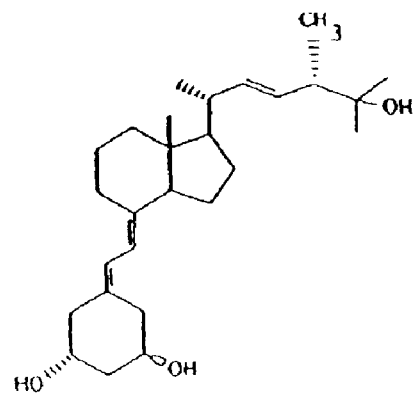
Figure 1:
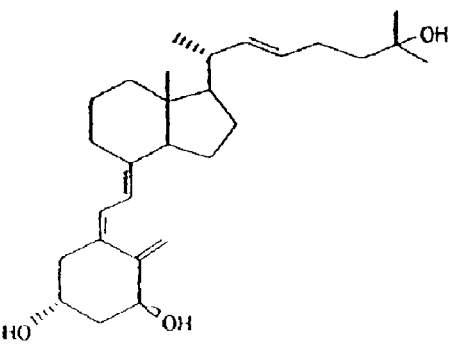
Figure 1:
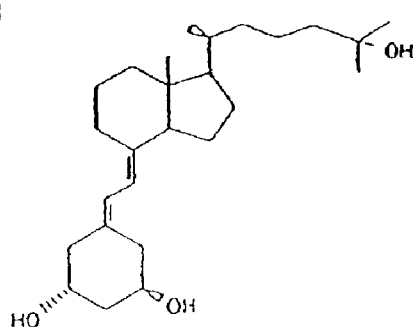
Figure 1:
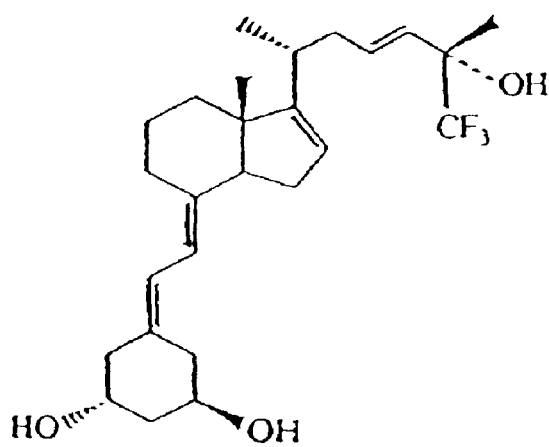
Figure 1:
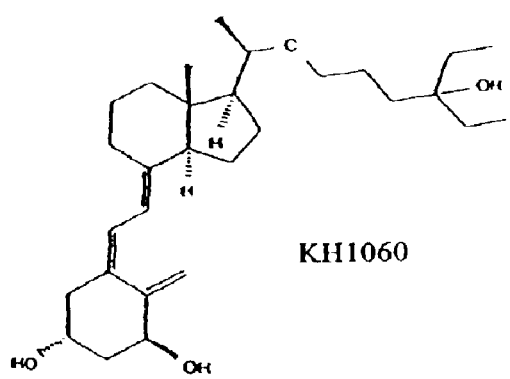
Figure 2:
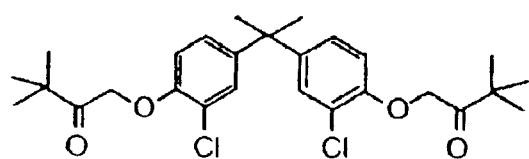
FIG. 2 depicts five nonsecosteroidal vitamin D compounds (mimics) useful in the present invention.
Figure 2:
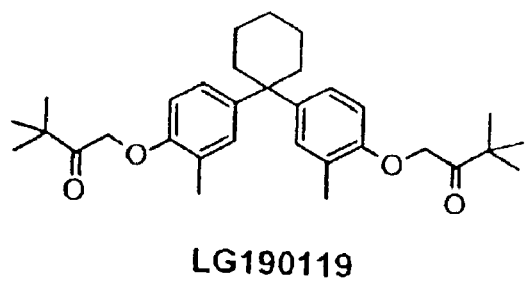
Figure 2:
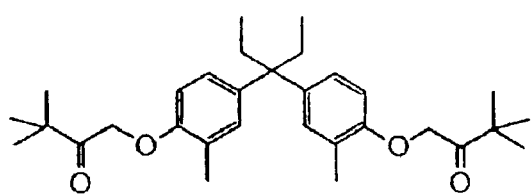
Figure 2:
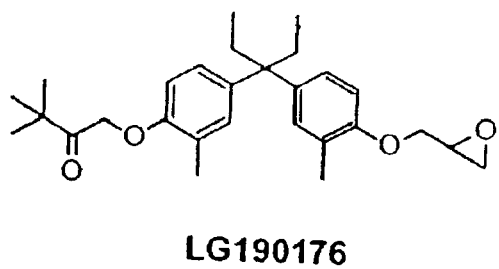
Figure 2:
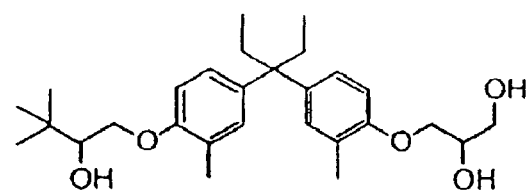

The present invention relates to therapeutic compositions and methods for the prevention treatment of IBD, and in particular the prevention and treatment of IBD in humans as well as other animals through the use of biologically active vitamin D compounds.

I. Intestinal Bowel Disease Risk Factors and Vitamin D

Intestinal Bowel Disease (IBD) encompasses both Crohn's Disease (CD) and Ulcerative Colitis (UC). CD and UC are distinct, but related polygenic disorders. Familial clustering of IBD strongly suggests that IBD susceptibility genes contribute to disease development. The relative risk of IBD among siblings of CD patients was 36.5 and among siblings of UC patients was 16.6, compared to the general population. Possible IBD susceptibility genes have been mapped to chromosomes 2, 3, 6, 7, 12 and 16. The identity and function of these susceptibility genes is unknown [See, Satangi et al., Clin. Sci. (Colch), May;94(5):473–8 (1998)].

Vitamin D stimulates bone mineralization, and there is evidence for poor bone mineralization in IBD patients [Andreassen et al., Scand. J. Gastroenterol., 32:1247–1255 (1997)]. Many reports found osteoporosis in greater than 40% of adult CD patients, while pediatric CD patients had significantly decreased bone length and mineral density compared to controls [Boot et al., Gut, 42:188–94 (1998)]. Neither malabsorption, nor steroid use explained the poor bone mineralization. Recently, an IBD susceptibility locus was mapped to chromosome 12 [Satangi et al., Clin. Sci. (Colch), May;94(5):473–8 (1998), and Duerr et al., Am. J. Hu. Gen., 63:95–100 (1998)]. This IBD susceptibility locus is in the same region as the vitamin D receptor and the 25-hydroxyvitamin D$_3$-1-α-hydroxylase genes [Labuda et al., J. Bone Min. Res. 7:1447–53 (1992)].

It is not intended that the present invention be limited to a particular mechanism of action. Indeed, an understanding of the mechanism is not necessary to make and use the present invention. However, it is believed that there may be a genetic defect in calcitriol synthesis, transport, or utilization which underlies a dual phenotype of decreased bone mineralization and susceptibility to IBD in some individuals. As such, the therapeutic affect of the administration of biologically active vitamin D compounds to patients may be achieved (at least in part) by compensating for these genetic defects.

Inheriting IBD susceptibility genes, however, is not sufficient for disease development. Environmental risk factors may be of equal or greater significance in determining IBD. IBD prevalence studies show a striking latitude gradient in the United States [Sonnenber et al., Gastroenterol. 102:1827 (1992)], and Europe [Shivananda et al., Gut, 39:690–7 (1996)]. The IBD incidence is high at northern latitudes and low at southern latitudes. For Example, there are 21 UC patients per 100,000 population aged 25–34 years in Norway [Moum et al., Scand. J. Gastroenterol., 31:362–6 (1996)], but only 1 UC patient per 100,000 population in Oman [Radhakrishnan et al., Digestion, 58:266–70 (1997)]. Therefore, while the IBD-determining environmental risk factor has not been identified yet, it appears to correlate strongly with latitude.

Vertebrates, including humans, obtain the majority of the daily requirement of vitamin D from casual exposure to sunlight [Holick, M. F., Am. J. Clin. Nutr., March;61(3 Suppl.):638S–645S (1995)]. UV light from the sun (282–310 nm) catalyzes a chemical photolysis reaction in the skin, converting 7-dehydrocholesterol to previtamin D$_3$, which spontaneously isomerizes to vitamin D$_3$ [Holick, M. F., Bone, 7:66–69 (1990)]. Vitamin D$_3$ is biologically inert, and must be activated by 25-hydroxylation in the liver and 1α-hydroxylation in the kidney to produce the vitamin D hormone 1α,25-dihyroxyvitamin D$_3$ (calcitriol) [Haussler et al., J. Endocrinol. 154:557–573 (1997)]. Above 52° N, there is insufficient sunlight intensity to catalyze vitamin D biosynthesis from October to April, whereas vitamin D biosynthesis occurs year-round below 34° N [Holick, M. F., Am. J. Clin. Nutr., March;61(3 Suppl.):638S–645S (1995)]. Vitamin D deficiency is common at northern latitudes. In one study, at 42° N, vitamin D deficiency affected 57% of a random population sample [Thomas et al., N. Eng. J. Med., 338:777–783 (1998)].

It is not intended that the present invention be limited to a particular mechanism of action. Indeed, an understanding of the mechanism is not necessary to make and use the present invention. However, it is believed that insufficient sunlight for vitamin D$_3$ biosynthesis may be a disease-determining environmental risk factor for IBD. As such, the therapeutic affect of the administration of biologically active vitamin D compounds to patients may be achieved by compensating for insufficient vitamin D biosynthesis in certain patients.

There is evidence that immune responses to GI tract microbes are involved in IBD pathology, but no specific microbe or microbial antigen has been implicated in IBD etiology [Fiocchi, C., Gastroenterology, 115:182–205 (1998)]. Antibodies and cells reactive with autoantigens have been detected, but their relevance to disease etiology is debated. T lymphocyte infiltration of the mucosa is characteristic of IBD; these infiltrating cells display activation markers [Pallone et al., Gut, 28:745–753 (1987), and broad specificity [Kaulfersch et al., Gastroenterology, 95:364–370 (1988)]. In CD, mucosal T cells display upregulated IL-2 receptors, and spontaneously produce IL-2 and IFN-γ [Breese et al., Immunology, 78:127–31 (1993)]. Moreover, CD mucosal cells spontaneously secrete IL-12 [Monteleone et al., Gastroenterol., 112:1169–78 (1997)]. These observations, together with the consistent finding of upregulated proinflammatory cytokines in IBD mucosa [Fiocchi, C., Gastroenterology, 115:182–205 (1998)], has suggested the hypothesis that IBD represents a dysregulated, T helper type 1 (Th1) driven immune response to the constant antigenic stimulation in the gut, with tissue damage being attributable to inflammatory mediators [Powrie, F., Immunity, 3:171–74 (1995)]. The opposing anti-inflammatory responses that maintain tolerance to enteric antigens appear to be dysfunctional in IBD.

Knockout animal models in the cytokine genes IL-2 [Sadlack et al., Cell, 75:253–61 (1993)], IL-10 [Kuhn et al. Cell, 75:63–74 (1993)], and TGF-β1 [Shull et al., Nature, 359:693 (1992)] all spontaneously develop a chronic IBD that shares histopathological features with human IBD. The T cell receptor (TCR) α mutant, TCR β mutant, and class II major histocompatibility complex (MHC) mutant mice also develop spontaneous IBD [Mombaerts et al., *Cell.* October 22;75(2):274–82 (1993)]. In these and other animal models of IBD, Th1 cells have been implicated in disease pathology [Berg et al., *J. Clin. Invest.* 98:1010–20 (1996)], while cells producing TGF-β have a particularly important regulatory role as suppressors of unchecked, Th1-driven inflammatory colitis [Powrie et al., *J. Exp. Med.* 183:2669–74 (1996)].

It has been shown that calcitriol is a potent and selective inhibitor of autoimmune disease in mice. For example, calcitriol administered to mice blocked disease induction for EAE (experimental autoimmune encephalomyelitis) [Cantorna et al., *Proc. Natl. Acad. Sci. USA*, 93:7861–7864 (1996)], Lyme arthritis and collagen induced arthritis [Cantorna et al., *J. Nutr.* 128:68–72 (1998)]. Furthermore, administering calcitriol to animals before EAE induction, or to animals with stage 1 EAE, arrested the clonal expansion of Th1 cells producing IFN-γ and TNF-α, and stimulated an increase in transcript accumulation for anti-inflammatory cytokines TGF-β1 and IL-4, in the central nervous system and lymph nodes [Cantorna et al., *J. Immunol.* 160:5314–5319 (1998)]. It has been shown that cells producing TGF-β1 have a crucial regulatory role as opponents of unchecked, Th-1 driven inflammatory responses [Shull et al., *Nature* 359:693 (1992), and Powrie et al., *J. Exp. Med.* 183:2669–74 (1996)].

It is not intended that the present invention be limited to a particular mechanism of action. Indeed, an understanding of the mechanism is not necessary to make and use the present invention. However, it is believed that the administration of calcitriol increases TGF-β1 expression, thus stimulating a therapeutic anti-inflammatory response in subjects with inflammatory bowel diseases.

II. Treatment of Vitamin D Responsive Diseases with Biologically Active Vitamin D Compounds The present invention contemplates the prevention and treatment of Inflammatory Bowel Disease, as well as other vitamin D responsive diseases, in a subject through the use of biologically active vitamin D compounds. Various forms of treatment and dosages are contemplated, as well as the avoidance of the development of the symptoms of hypercalcemia.

A. Treatment and Dosage

The present invention contemplates both the treatment and prevention of IBD, as well as other vitamin D responsive disease, in humans as well as other animals (e.g. mammals) with biologically active vitamin D compounds in therapeutic amounts. It is not intended that the present invention be limited to particular dosages. A broad range of dosages for the therapeutic administration of the biologically active vitamin D compounds are contemplated. In certain embodiments, a preferred dose of the biologically active vitamin D compound for the present invention is the maximum that a patient can tolerate and not develop serious hypercalcemia. If the biologically active vitamin D compound is not a 1α-hydroxy compound, a daily dose between 1.0 and 100 μg per day per 160 pound patient may be administered, while a particularly advantageous daily dose is between 5.0 and 50 μg per day per 160 pound patient. If the biologically active vitamin D compound is a 1α-hydroxy compound, a daily dose of between 0.1 and 20 μg per day per 160 patient may be administered, while a preferred dose is between 0.5 and 10 μg per day per 160 pound patient. In a particularly preferred embodiment, the dose is between 3–10 μg per day. In general, a preferred dose is the highest amount of the biologically active vitamin D compound the patient can tolerate. Also preferred are doses of the biologically active vitamin D compound that are greater than the maximum the subject can normally tolerate (e.g. co-administration of IL-10 and a biologically active vitamin D compound allowing such "above maximum" doses to be administered without harming the subject). The dose is preferably divided between two, three, four or five treatments within a 24 hour period.

In the United States, the accepted safe dose of 1,25(OH$_2$) D$_3$ and 19-nor-21-epi-1,25(OH$_2$)D$_3$ in patients having normal calcium intakes is between 0.5 and 15 μg per day for 1,25(OH$_2$)D$_3$, and is 10–20 μg/day for 19-nor-1,25-(OH)$_2$D$_2$. A preferred dose for patients with normal calcium intakes is between 0.5 and 0.75 μg per day for a 160 pound patient depending on the compound administered. Patients on a low calcium diet, and/or if the compounds are administered at night (or if administered with IL-10), may tolerate more per day (e.g., 3 μg more per day). Therefore, in certain embodiments of the present invention, treatment with biologically active vitamin D compounds is administered in as high a dose as the patient can tolerate without developing symptoms of hypercalcemia. In this regard, high doses (e.g. 3–10 μg per day) are administered. However, for 19-nor-1, 25(OH$_2$)D$_2$ and 24-homo-22-dehydro-22E-1α,25(OH$_2$)D$_3$ the safe dosage range is 10–20 μg per day per 160 pound patient (or more if administered with IL-10).

A determination of whether a patient is benefiting from treatment (i.e. wherein symptoms are reduced), may be performed by monitoring the qualitative and quantitative symptoms of IBD (or other vitamin D responsive disease). Qualitative symptoms which may monitored include, but are not limited to, abdominal pain, diarrhea, rectal bleeding, weight loss, fever, loss of appetite, dehydration, anemia, and malnutrition. Quantitative symptoms which may be monitored include, but are not limited to, weight loss, fever, and anemia (using a blood test). A successful treatment is indicated wherein the symptoms of IBD (or other vitamin D responsive disease) are reduced. Preferably, treatment should continue as long as IBD, or other vitamin D responsive disease, symptoms are suspected or observed.

A determination of whether a subject would benefit from prophylactic treatment of IBD, or other vitamin D responsive disease, is determined by assessing various risk factors. In other words, a determination of whether a subject is at risk for IBD, or other vitamin D responsive disease, is made. It is not intended that the present invention be limited to particular risk factors. Indeed, a variety of risk factors may be monitored, including, but not limited to; genetic predisposition, amount of sunlight the patient normally receives, the age of the patient (common in young people), nationality (common in U.S, England, and Northern Europe), and ancestry/race (common in people of Jewish decent). Patients at risk are prophylactically administered the therapeutic compositions of the present invention to delay or prevent the onset of symptoms of IBD, or other vitamin D responsive disease.

B. Hypercalcemia

As mentioned above, a preferred dose of vitamin D compound for the present invention is the maximum that a patient can tolerate and not develop serious hypercalcemia. Another preferred embodiment is more than the maximum amount the patient can typically tolerate when the biologically active vitamin D compound is administered alone (e.g. providing more than the maximum amount of a biologically active vitamin D compound than the subject can typically handle in combination with IL-10). Hypercalcemia is a risk in the administration of biologically active vitamin D compounds (e.g. calcitriol) because the major physiological function of vitamin D is to maintain extracellular calcium levels within a very limited normal range for normal cellular and metabolic processes (including neuromuscular function and bone mineralization). To maintain serum calcium levels, calcitriol primarily increases intestinal absorption of dietary calcium and phosphate, and when required, mobilizes bone calcium. Thus, calcitriol has a potent calcemic effect (i.e. generates a calcemic response in a subject). Therefore, the primary concern associated with administering calcitriol or its analogues to subjects (e.g. humans or other mammals) is elevated serum calcium (hypercalcemia) and phosphate levels, a condition accompanied by a corresponding increase in urinary calcium excretion (hypercalcuria).

The toxicity of vitamin D compounds can have serious consequences for renal function; prolonged hypercalcemia can result in calcium deposition in the kidneys (nephrocalcinosis), kidney stones (nephrolithiasis), and ultimately in renal dysfunction leading to uremia. Vitamin D intoxication may also have serious consequences for neurological functions. In severe hypercalcemia, the threshold for excitation of nerve and muscles is increased, resulting in clinical manifestations of muscle weakness, lethargy, and even coma. Gastrointestinal manifestations of vitamin D intoxication include constipation, anorexia, nausea, and vomiting, with subsequent fluid loss which exacerbates the hypercalcemic crisis. Hypercalcemia can also affect cardiovascular functioning, including shortening of the QT interval, hypotension, and arrhythmias. Therefore, it is important to monitor the development of hypercalcemia in patients receiving biologically active vitamin D compounds. Hypercalcemia may be monitored in a patient by measuring the terminal serum calcium levels.

One way hypercalcemia risks can be minimized in the treatment of subjects with biologically active vitamin D compounds is by performing dose-response studies in an animal model of IBD (e.g. DS-induced mice, carageenan-induced guinea pigs, or IL-2, TGF-B1, TCR, MHC, or IL-10 knockout mice) employing a chosen biologically active vitamin D compound. In preferred embodiments, the animal employed is an IL-10 knockout mouse. In certain embodiments, these studies involve assaying the level of the biologically active vitamin D compound in the serum and correlating dietary dose of this compound to biologically efficacy and the symptoms of hypercalcemia such that the minimum effective dose is determined. Another method of minimizing the risks of hypercalcemia involves administering the biologically active vitamin D compound using timed drug release methods (e.g. suppository or transdermal patch) or "slow release" biologically active vitamin D derivatives (See, U.S. Pat. No. 5,952,317, hereby incorporated by reference).

While it is not intended that the present invention be limited to a particular mechanism of action, and indeed, an understanding of the mechanism is not necessary to make and use the present invention, it is believed that the use of a transdermal patch reduces the risk of hypercalcemia (caused by mobilization of calcium across the intestinal wall) by preventing a delivery 'spike' of the biologically active vitamin D compound. A transdermal patch is believed to deliver a continuous, lower dosage stream of the biologically active vitamin D compounds such that a spike (total dosage all at once) which could cause a severe increase in the mobilization of calcium across the intestine wall, is avoided.

Also, while it is not intended that the present invention be limited to a particular mechanism of action, and indeed, an understanding of the mechanism is not necessary to make and use the present invention, it is believed that the co-administration of IL-10 serves to counteract the calcemic affect of biologically active vitamin D compounds. As such, co-administering IL-10 to a subject helps prevent hypercalcemia from developing in the subject, and allows higher doses of biologically active vitamin D compounds to be tolerated by the subject. Importantly, this reduces the risk of using biologically active vitamin D compounds to treat vitamin D responsive diseases (e.g. risk of patients dyeing from hypercalcemia), and also allows subjects to tolerate the higher doses that may be required to effectively treat certain vitamin D responsive diseases. Co-administration of IL-10 may also allow, for example, subjects to maintain a higher level of calcium intake during the course of treatment than would otherwise be possible without IL-10 administration.

III. Biologically Active Vitamin D Compounds

As defined above, biologically active vitamin D compounds of the present invention encompass vitamin D compounds which are biologically active in vivo, or are acted upon in a subject (i.e. host) such that the compound becomes active in vivo. Examples of such compounds include: vitamin D, $1,25(OH_2)D_3$ and analogs thereof (e.g. $1\alpha$-hydroxyvitamin $D_3$ ($1\alpha$-OH-$D_3$), $1,25$-dihydroxyvitamin $D_2$ ($1,25$-$(OH)_2D_2$), $1\alpha$-hydroxyvitamin $D_2$ ($1\alpha$-OH-$D_2$), 26,27-hexafluoro-1,25-dihydroxyvitamin $D_2$ ($F_6$-1,25-$(OH)_2D_3$), 19-nor-1,25-dihydroxyvitamin $D_2$ (19-nor-1,25-$(OH)_2D_2$), 1,25-dihydroxy-24(E)-dehydro-24-homo-vitamin $D_3$ (1,25-$(OH)_2$-24-homo$D_3$), 19-nor-1,25-dihydroxy-21-epi-vitamin $D_3$ (19-nor-1,25-$(OH)_2$-21-epi-$D_3$), $1\alpha,25$ dihydroxyvitamin $D_3$ triacetate and 25-acetyl-$1\alpha,25$ dihydroxyvitamin $D_3$, 1,25-dihydroxy-24-homo-22-dehydro-22E-vitamin $D_3$, 19-nor-1,25-dihydroxy-24-homo-22-dehydro-22E-vitamin $D_3$, $1\alpha,25$-$(OH)_2$-24-epi-$D_2$, $1\alpha,25$-$(OH)_2$-24a-Homo-$D_3$,$1\alpha,25$-$(OH)_2$-24a-Dihomo-$D_3$, $1\alpha,25$-$(OH)_2$-19-nor-$D_3$, and 20-epi-24-homo-$1\alpha,25$-$(OH)_2$-$D_3$). [See, U.S. Pat. Nos. 5,716,946 and 5,891,865, and Bouillon et al., Endocr Rev. April;16(2):200–57 (1995), all incorporated herein by reference].

The present invention also contemplates other biologically active vitamin D compounds which may be represented by various functional classes. The first functional class are vitamin D compounds which exhibit significant activity in vivo as inhibitors of autoimmunity (e.g. multiple sclerosis or experimental autoimmune encephalomyelitis, type one diabetes, arthritis or lyme arthritis or collagen-induced arthritis, glomerulonephritis, thyroiditis, systemic lupus erythematosus), and which exhibit calcemic activity in vivo that is less than or equal to but not more than calcitriol (i.e. 1,25$(OH)_2D_3$). Examples of this class include, but are not limited to, $1\alpha,25$-dihydroxy-16ene-vitamin $D_3$ and $1\alpha,25$-dihydroxy-24-oxo-16ene-vitamin $D_3$ [See, Lemire et al., Endocrinology, 135:2818–2821, (1994)]; $1\alpha,24R$-dihydroxy-vitamin $D_3$ [See, Koizumi et al., Int. Arch. Allergy Appl. Immunol., 77:396–404 (1985); $1\alpha,25$-dihydroxy-22-oxa-vitamin $D_3$ [See, Abe et al., Endocrinology, 124:2645–2647 (1989)]; 20-Epi-22-oxa-24a,26a,27a-trihomo-$1\alpha,25$-dihydroxy-vitamin $D_3$ [Lillerang et al., Clin. Exp. Immunol., 88:301–306 (1992)]; and 19-nor-1,25-dihydroxy-vitamin $D_3$ [See, U.S. Pat. No. 5,716,946, herein incorporated by reference].

The second functional class are vitamin D compounds which exhibit significant activity in vivo as an inhibitor of transplanted cells, tissue, or organ rejection (e.g. skin graft, heart graft, islet graft, etc.), and exhibit calcemic activity in vivo that is less than or equal to calcitriol. Examples of this class include, but are not limited to, 1,25-dihydroxy-16ene-vitamin $D_3$ [See, Lemire et al., Transplantation, 54:762–763

(1992)]; and 20-Epi-22-oxa-24a,26a,27a-trihomo-1,25-dihydroxy-vitamin $D_3$ [See, Veyron et al., *Transplant Immunol.*, 1:72–76 (1993)].

The third functional class are vitamin D compounds which exhibit significant activity in an in vitro cell differentiation assay (e.g. HL-60, U-937, NB4, etc.) and exhibit in vivo calcemic activity that is less than or equal to calcitriol. Examples of this class include, but are not limited to 1,25-dihydroxy-16,23E-diene-26-trifluoro-19-norcholecalciferol [See, Asou et al., *Blood*, 92:2441–2449 (1998)]; 11α-vinyl-1α,25-dihydroxy-vitamin $D_3$ [See, Bouillon et al., *J. Biol. Chem.*, 267:3044–3051 (1992)]; 1α,25-dihydroxy-16ene-23yne-vitamin $D_3$ [Norman et al., *Cancer Res.*, 50:6857–6864 (1990)]; 24-homo-22-dehydro-22E-1α,25-dihydroxy-vitamin $D_3$ and 1,25-dihydroxy-22ene-24-homo-vitamin $D_3$ [Perlman et al., *Biochemistry*, 29:190–196).

The fourth functional class are vitamin D compounds (mimics) which exhibit significant activity as an activator of the nuclear vitamin D receptor in an in vitro transcriptional activation assay, while also exhibiting a binding affinity for the serum vitamin D binding protein that is less than or equal to calcitriol. An example of this class includes, but is not limited to LG190090, LG190119, LG190155, LG190176, and LG1900178 [See, Boehm et al., Chemistry & Biology 6:265–275 (1999)].

Other biologically active vitamin D compounds are contemplated for use in the present invention, including, but not limited to, compounds described in: U.S. Pat. No. 5,936,105 (incorporated herein by reference), U.S. Pat. No. 5,932,565 (incorporated herein by reference), U.S. Pat. No. 5,929,056 (incorporated herein by reference), U.S. Pat. No. 5,905,074 (incorporated herein by reference), U.S. Pat. No. 5,902,806 (incorporated herein by reference), U.S. Pat. No. 5,883,271 (incorporated herein by reference), U.S. Pat. No. 5,877,168 (incorporated herein by reference), U.S. Pat. No. 5,872,140 (incorporated herein by reference), U.S. Pat. No. 5,811,562 (incorporated herein by reference), U.S. Pat. No. 5,786,347 (incorporated herein by reference), U.S. Pat. No. 5,756,733 (incorporated herein by reference), U.S. Pat. No. 5,716,945 (incorporated herein by reference), and U.S. Pat. No. 5,710,142 (herein incorporated by reference). Other biologically active compounds useful in the practice of the present invention are indicated by the following formulas:

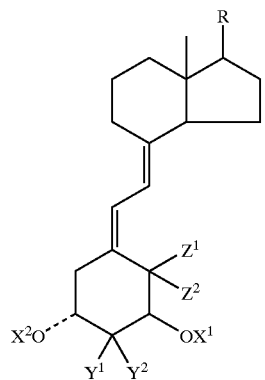

wherein $X^1$ and $X^2$ are each selected from the group consisting of hydrogen and acyl;
wherein $Y^1$ and $Y^2$ can be H, or one can be O-aryl or O-alkyl while the other is hydrogen and can have β or α configuration; $Z^1$ and $Z^2$ are both H, or $Z^1$ and $Z^2$ taken together are $CH_2$; and
wherein R is an alkyl, hydroxyalkyl or fluoroalkyl group, or R may represent the following side chain:

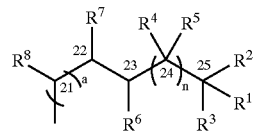

wherein (a) may have an S or R configuration and wherein $R^1$ represents hydrogen, hydroxy or O-acyl, $R^2$ and $R^3$ are each selected from the group consisting of alkyl, hydroxyalkyl and fluoroalkyl, or, when taken together represent the group—$(CH_2)_m$—where m is an integer having a value of from 2 to 5, $R^4$ is selected from the group consisting of hydrogen, hydroxy, fluorine, O-acyl, alkyl, hydroxyalkyl and fluoroalkyl, $R^5$ is selected from the group consisting of hydrogen, hydroxy, fluorine, alkyl, hydroxyalkyl and fluoroalkyl, or, $R^4$ and $R^5$ taken together represent double-bonded oxygen, $R^6$ and $R^7$ taken together form a carbon—carbon double bond and $R^8$ may be H or $CH_3$, and wherein n is an integer having a value of from 1 to 5, and wherein the carbon at any one of positions 20, 22, or 23 in the side chain may be replaced by an O, S, or N atom.

As used herein, the term "alkyl" signifies an alkyl radical of 1 to 5 carbons in all isomeric forms, such as methyl, ethyl, propyl, isopropyl, butyl, isobutyl, pentyl, etc., and the terms "hydroxyalkyl" and "fluoroalkyl" refer to such an alkyl radical substituted by one or more hydroxy or fluoro groups respectively. The term "acyl" means an aliphatic acyl group of 1 to 5 carbons, such as formyl, acetyl, propionyl, etc. or an aromatic acyl group such as benzoyl, nitrobenzoyl or halobenzoyl. The term "aryl" signifies a phenyl-, or an alkyl-, nitro- or halo-substituted phenyl group.

The present invention also contemplates "slow release" derivatives of the biologically active vitamin D compounds of the present invention (See U.S. Pat. No. 5,952,317, incorporated herein by reference). The following formula describes these various derivatives:

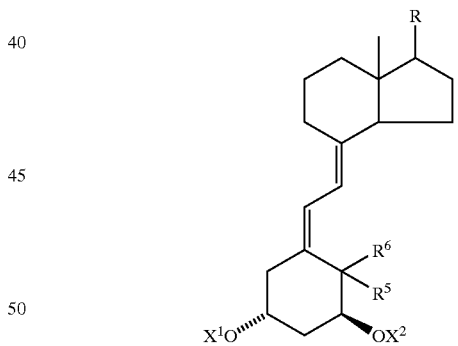

where $R^5$ and $R^6$ each represent hydrogen, or taken together $R^5$ and $R^6$ represent a methylene group.
The side chain group R in the above-shown structure represents a steroid side chain of the structure below:

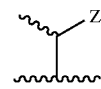

where the stereochemical center (corresponding to C-20 in steroid numbering) may have the R or S configuration, (i.e., either the natural configuration about carbon 20 or the opposite unnatural configuration), and where Z is selected from Y, —OY, —$CH_2$ OY, —C≡CY and —CH=CHY, where the double bond may have the cis or trans geometry, and where Y is selected from a radical of the structure:

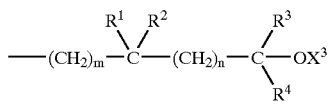

where m and n, independently, represent the integers from 0 to 5, where $R^1$ is selected from hydrogen, $OX^4$, fluoro, trifluoromethyl, and $C_{1-5}$-alkyl, which may be straight chain or branched and, optionally, bear a hydroxy substituent, and where $R^2$ is selected from hydrogen, fluoro, trifluoromethyl and $C_{1-5}$ alkyl, which may be straight-chain or branched, and optionally, bear a hydroxy substituent, and where $R^3$ and $R^4$, independently represent trifluoromethyl or $C_{1-5}$alkyl, which may be straight chain or branched and, optionally, bear a hydroxy substituent, and where $R^1$ and $R^2$, taken together, represent an oxo group, or an alkylidene group, $=CR^2R^2$, or $=CR^2R^3$, or the group —$(CH_2)_p$—, where p is an integer from 2 to 5, and where $R_3$ and $R_4$, taken together, represent the group —$(CH_2)_q$—, where q is an integer from 2 to 5. In the above-shown structures $X^1$, $X^2$ and $X^4$ independently represent hydrogen, an acyl group or a hydrocarbyloxycarbonyl group, and $X^3$ represents an acyl group or a hydrocarbyloxycarbonyl group, as previously defined herein.

In order to evaluate whether a given vitamin D analog or slow release derivative is suitable as a biologically active vitamin D compound useful for the treatment of IBD, an animal model of IBD (e.g. DS-induced mice, carageenan-induced guinea pigs, or IL-2, TGF-β1, TCR, MHC, IL-10 knockout mice, HLA-B27/β2m transgenic rat, trinitrobenzene sulfonic acid induced colitis in rodents, or spontaneous IBD in cotton-top tamarin colonies held in temperate climates) may be employed [See also, Bouillon et al., *Endocr Rev.* April;16(2):200–57 (1995)]. The inhibition of both induction and established IBD, as well as risk of hypercalcemia are evaluated. Useful biologically active vitamin D compounds reduce the symptoms of IBD. Especially useful biologically active vitamin D compounds reduce the symptoms of IBD, or other vitamin D responsive diseases, and do not cause substantial hypercalcemia at therapeutic dosages.

IV. Therapeutic Preparations and Combinations

In some embodiments, the present invention contemplates using therapeutic compositions of biologically active vitamin D compounds and therapeutic compositions of IL-10 (or IL-4, or TNFα inhibitor). It is not intended that the present invention be limited by the particular nature of the therapeutic composition. For example, such compositions can be provided together with physiologically tolerable liquids, gels, solid carriers, diluents, adjuvants and excipients (and combinations thereof).

In addition, biologically active vitamin D compounds may be used together with other therapeutic agents, including, but not limited to, salicylates, steroids, immunosuppressants, antibodies or antibiotics. In some embodiments, biologically active vitamin D compounds are used together with IL-10. In other embodiments, biologically active vitamin D compounds are used together with IL-4. In certain embodiments, biologically active vitamin D compound are used together with anti-TNFα antibody.

Particular therapeutic agents which may be used with the biologically active vitamin D compounds of the present invention include, but are not limited to, the following agents: azobenzene compounds (U.S. Pat. No. 4,312,806, incorporated herein by reference), benzyl-substituted rhodamine derivatives (U.S. Pat. No. 5,216,002, incorporated herein by reference), zinc L-carnosine salts (U.S. Pat. No. 5,238,931, incorporated herein by reference), 3-phenyl-5-carboxypyrazoles and isothiazoles (U.S. Pat. No. 5,294,630, incorporated herein by reference), IL-10 (U.S. Pat. No. 5,368,854, incorporated herein by reference), quinoline leukotriene synthesis inhibitors (U.S. Pat. No. 5,391,555, incorporated herein by reference), 2'-halo-2'deoxy adenosine (U.S. Pat. No. 5,506,213, incorporated herein by reference), phenol and benzamide compounds (U.S. Pat. No. 5,552,439, incorporated herein by reference), tributyrin (U.S. Pat. No. 5,569,680, incorporated herein by reference), certain peptides (U.S. Pat. No. 5,756,449, incorporated herein by reference), omega-3 polyunsaturated acids (U.S. Pat. No. 5,792,795, incorporated herein by reference), VLA-4 blockers (U.S. Pat. No. 5,932,214, incorporated herein by reference), prednisolone metasulphobenzoate (U.S. Pat. No. 5,834,021, incorporated herein by reference), cytokine restraining agents (U.S. Pat. No. 5,888,969, incorporated herein by reference), and nicotine (U.S. Pat. No. 5,889,028, incorporated herein by reference).

The therapeutic compositions of the present invention can be administered to mammals for veterinary use, such as with domestic animals and non-human primates, and clinical use in humans in a manner similar to other therapeutic agents. In general, the dosage required for therapeutic efficacy varies according to the type of use and mode of administration, as well as the particularized requirements of individual hosts. A preferred dose of the biologically active vitamin D compounds of the present invention is the maximum that a patient can tolerate and not develop serious hypercalcemia. Other preferred doses are those greater than the maximum that can ordinarily be tolerated (e.g. combination therapy of IL-10 and at least one biologically active vitamin D compound). The attending medical professional is capable of determining the therapeutically effective dosage based on the characteristics of the subject (e.g., gender, age, weight, amount of calcium in diet, etc.).

With respect to the mode of administration, in some embodiments the biologically active vitamin D compounds, and IL-10 compositions, (and therapeutic compositions thereof) are administered intravenously, intramuscularly, subcutaneously, intradermally, intraperitoneally, intrapleurally, intrathecally, orally, rectally or topically. In some embodiments, formulations for such administrations may comprise an effective amount of the biologically active vitamin D compound, and/or an effective amount of IL-10, in sterile water or physiological saline. In other embodiments, formulations for such administrations may comprise an effective amount of the biologically active vitamin D compound, and/or IL-10, in an organic solvent (e.g. ethanol, vegetable oil, or glycerol).

On the other hand, therapeutic compositions may contain such normally employed additives as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions typically contain 1%–95% of active ingredient, preferably 2%–70%.

The biologically active vitamin D compounds of the present invention, and the IL-10 compositions, can also be mixed with diluents or excipients which are compatible and physiologically tolerable. Suitable diluents and excipients are, for example, water, saline, dextrose, glycerol, or the like, and combinations thereof. In addition, if desired, the compositions may contain minor amounts of auxiliary substances such as wetting or emulsifying agents, stabilizing or pH buffering agents.

In some embodiments, the therapeutic compositions of the present invention are prepared either as liquid solutions or suspensions, as sprays, or in solid forms. Oral formulations usually include such normally employed additives such as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained release formulations, or powders, and typically contain 1%–95% of active ingredient, preferably 2%–70%. One example of an oral composition useful for delivering the therapeutic compositions of the present invention is described in U.S. Pat. No. 5,643,602 (incorporated herein by reference).

Additional formulations which are suitable for other modes of administration, such as topical administration, include salves, tinctures, creams, lotions, transdermal patches, and suppositories. For salves and creams, traditional binders, carriers and excipients may include, for example, polyalkylene glycols or triglycerides. One example of a topical delivery method is described in U.S. Pat. No. 5,834,016 (incorporated herein by reference). Other liposomal delivery methods may also be employed. Examples of this type of delivery of the biologically active vitamin D compounds of the present invention include U.S. Pat. Nos. 5,851,548 and 5,711,964 (both incorporated herein by reference).

In certain particularly preferred embodiments, the therapeutic composition comprising biologically active vitamin D compounds, and/or IL-10, is administered via a transdermal patch. A transdermal patch optimally includes a therapeutically effective amount of the biologically active vitamin D compounds of the present invention. While not limited to any mechanism, it is believed that transdermal delivery would provide a continuous supply of the vitamin D compound, maintaining the vitamin D receptor occupancy at a stable, optimal level, to achieve the desired biological effect. This is in contrast to other modes of delivery (e.g. oral or intravenous) which could provide a peak hormone concentration (spike) shortly after delivery, which would subsequently decline (leading to cyclical hormone occupancy and peak concentrations stimulating calcium absorption, bone resorption, or soft tissue calcification). Transdermal delivery may also bypass delivery of the vitamin D compounds to the intestine, decreasing binding to the vitamin D receptors in the intestinal epithelial cells. This in turn may decrease stimulation of intestinal calcium absorption, and decrease the calcemic effect of the vitamin D compound. Transdermal delivery may also be preferred because intestinal physiology is disturbed in patients with IBD, which may alter uptake of the vitamin D compound in a patient-specific, non-predictable manner (making dose determination difficult for other modes of administration such as oral delivery). Transdermal delivery may be more convenient than other modes of delivery (especially for children), and could increase patient compliance.

One example of a transdermal patch for delivering therapeutics employs a polyurethane acrylic copolymer (U.S. Pat. No. 4,638,043, incorporated herein by reference). Another example of a transdermal patch employs polymers and vitamin E (U.S. Pat. No. 5,830,505, incorporated herein by reference). A third example of a transdermal patch employs an adhesive matrix of silicone or polyisobutylene or both (U.S. Pat. No. 5,876,746, incorporated herein by reference). Other transdermal patches are known in the art, and are contemplated as modes for delivering the biologically active vitamin D compounds of the present invention.

In other preferred embodiments, enteric formulations are employed. The covering may comprise an enteric coating or a capsule. The terms "enteric coating" or "enteric film" are used interchangeably and refer to a material or compound which is resistant to acid pH (i.e., an acid-resistant compound), such as that found in the stomach. An enteric coating when applied to a solid inhibits the dissolution of the solid in the stomach.

Standard techniques are known to the art for the encapsulation of solid compositions. These techniques include microencapsulation of a solid composition wherein an enteric coating is applied to the solid composition. The coated material may be delivered orally to a subject by suspending the microencapsulated particles in pharmaceutical suspension solutions known to the art. The capsule would preferably have the characteristic of being resistant to dissolution in the stomach and being capable of dissolving in the intestines. Numerous suitable capsule formulations are available to the art; in addition standard techniques are available for the filling of capsules including the use of inert filler materials to provide sufficient bulk of the filling of a capsule with a therapeutic composition in a solid form. In addition to the use of encapsulated compositions, the biologically active vitamin D compounds, and the IL-10 compositions, may be delivered orally in tablet or pill form. The biologically active vitamin D compounds, and the IL-10 compositions, may be combined with inert materials to provide sufficient bulk for the pressing of the tablet or pill. Once formed, the tablet or pill may then be coated with an enteric film to prevent dissolution in the stomach and to enhance dissolution in the intestines.

V. IL-10 and Biologically Active Vitamin D Compounds

The present invention provides methods of treating subjects with biologically active vitamin D compounds and IL-10. In some embodiments of the present invention, subject that are known (or determined to be) IL-10 deficient are treated for IBD, or other vitamin D responsive disease, with therapeutic compositions comprising a biologically active vitamin D compound and IL-10. In other embodiments, IL-10 deficient subjects are treated with combination therapy of IL-10 and a biologically active vitamin D compound (e.g. separate administration of IL-10 and a biologically active vitamin D therapy). In some embodiments IL-10 is administered to a subject in a protein form (e.g. intravenous injection). In other embodiments, the gene expressing IL-10 is administered to the subject such that IL-10 is expressed in the subject (e.g. Rogy et al., *Human Gene Therapy*, 11:1731–1741, August 2000, herein incorporated by reference, describing a clinical protocol involving the IL-10 gene complexed to cationic lipids that are administered subcutaneously and submucosely in the rectal and perianal region of patients with IBD of the rectum). Further examples of IL-10 preparation, production, and subject dosages are provided in U.S. Pat. No. 5,945,097 to Cutler, U.S. Pat. No. 5,776,451 to Hsu et al., and Fedorak et al, *Gastroenterology*, 119:1473–82, 2000, all of which are hereby incorporated by reference. Examples of daily IL-10 dosages for a subject include; 1–100 micrograms/kg/day, 1–15 micrograms/kg/day, or approximately 8 micrograms/kg/day. In particularly preferred embodiments, approximately 5 micrograms/kg/day of IL-10 is provided to a subject (e.g. for at least 21 days).

In some embodiments, the present invention contemplates screening subjects for the presence of IL-10 prior to the administration of biologically active vitamin D compounds (e.g. prior to administration of biologically active vitamin D compounds to subjects with IBD or at risk for IBD, or any other disease where biologically active vitamin D compounds are administered for treatment). Screening subjects for the presence of IL-10 may be performed, for example, by obtaining a biological sample (e.g. blood sample, tissue sample, or other bodily fluid) from the subject and contacting the sample with an IL-10 binding ligand. Examples of binding ligands includes, but is not limited to, polyclonal antibodies, monoclonal antibodies, nucleic acid sequences, and IL-10 receptors (e.g. expressed recombinantly). U.S. Pat. No. 6,028,186 to Tasset et al. (hereby incorporated by reference) provides nucleic acid molecules (isolated by the SELEX procedure) capable of binding IL-10. Also, U.S. Pat. No. 5,231,012 to Mosmann et al. (hereby incorporated by reference) describes antibodies to IL-10 (e.g. polyclonal and monoclonal antibodies). IL-10 detection kits are also available commercially (e.g. PromoCell, which supplies a human IL-10 ELISA kit). Any method of determining the IL-10 status of a subject is useful in the present invention. In this regard, in some embodiments, subjects identified as IL-10 deficient may be administered both IL-10 and a biologically active vitamin D compound in order to treat (or prevent) IBD, or other vitamin D responsive diseases.

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); µM (micromolar); mol (moles); mmol (millimoles); µmol (micromoles); nmol (nanomoles); pmol (picomoles); g (grams); mg (milligrams); µg (micrograms); ng (nanograms); l or L (liters); ml (milliliters); µl (microliters); cm (centimeters); mm (millimeters); µm (micrometers); nm (nanometers); DS (dextran sulfate); ° C. (degrees Centigrade); and Sigma (Sigma Chemical Co., St. Louis, Mo.).

EXAMPLE 1

Calcitriol Inhibition of IBD Induction

This Example describes the inhibition of IBD induction in mice with calcitriol. Two types of mouse models are utilized. The fist group is the widely used DS-induced murine model, which reflects the involvement of enteric microbes, innate immunity, and non-specific inflammation in IBD. Mouse strains vary in their susceptibility to DS-induced IBD [Mahler et al., *Am. J. Physiol.—Gastro. & Liver Physiol.*, 37 G: 544-G 551, (1998)], so the highly susceptible strains C3H/HeJ and C57BL/6J are employed. The second group of IBD models involves mice with targeted disruptions in immunologically relevant genes. In particular, the widely used IL-10 knockout on the C57BL/6J background is employed (i.e. C57BL/6J-IL-10 ko). An alternative to these C57BL/6J-IL-10 ko mice (not described in this Experiment), are mice with a homozygous IL-10 ko mutation on the mixed 129/O1axC57BL/6 genetic background. These two groups of mice are employed as described below to demonstrate the effect of calcitriol on the inhibition of IBD induction (See Table 1, overview of Experimental Groups).

TABLE 1

Experimental Groups.

| Group | Strain | Inducing agent | Treatment |
|-------|--------|----------------|-----------|
| 1 | C3H/HeJ | none | none |
| 2 | C3H/HeJ | DS | none |
| 3 | C3H/HeJ | DS | calcitriol |
| 4 | C3H/HeJ | DS | prednisolone |
| 5 | C57BL/6J | none | none |
| 6 | C57BL/6J | DS | none |
| 7 | C57BL/6J | DS | calcitriol |
| 8 | C57BL/6J | DS | prednisolone |
| 9 | 129/Ola x C57B1/6J-IL-10 ko | none | none |
| 10 | 129/Ola x C57BL/6J-IL-10 ko | none | calcitriol |
| 11 | 129/Ola x C57BL/6J-IL-10 ko | none | prednisolone |

A. Treatment of the Mice

The DS-induced IBD study (groups 1–8; Table 1) are treated as follows. Beginning on day 0 and continuing, groups of 10 mice are fed a purified diet without or with calcitriol (50 ng/day females; 200 ng/day males); this dose is based on dose-response studies in EAE [Cantorna et al., *J. Immunol.*, 160:5314–5319 (1998)]. The prednisolone-treated group is fed a purified diet with prednisolone (20 ng/day). These experimental diets have been published [Cantorna et al., *Proc. Natl. Acad. Sci.* USA, 97:7861–7864 (1996)], and are replenished each 2–3 days. On day 2, the mice are weighed and DS (3.5% wt/vol) is given in the drinking water on days 2–6 (Okayasu, et al., *Gastro.*, 98:694–702 (1990)]. The mice receive acidified drinking water without DS for days 7–22. On days 7, 11, 15, and 19, mice are weighed and stool samples are collected. A blood sample is collected on day 11. On day 22, mice are weighed, euthanized, and stool, blood, and colon samples are collected. The samples are analyzed as described below.

The mock-treated control mice in this Example are expected to show severe weight loss, bloody diarrhea (as evidenced by fecal hemoglobin), shortening of the colon and thickening of the colonic wall, mucosal ulceration, goblet cell loss, and crypt elongation and loss (as evidenced by histopathologic score), and inflammatory infiltration by lymphocytes, macrophages, neutrophils, and granulocytes (as evidenced by fecal lactoferrin and colonic myeloperoxidase activity) during IBD induction and progression. The calcitriol-treated mice exhibit significantly reduced incidence or severity of disease as compared to the mock-treated controls. With respect to severity, the calcitriol-treated mice exhibit significantly reduced weight loss, bloody diarrhea, shortening and thickening of the colon, histopathologic score, and inflammatory infiltration as compared to the mock-treated controls.

The spontaneous IBD study (groups 9–11; Table 1) are treated the same as the DS-induced mice, except purified diet feeding begins when the IL-10-ko mice are weaned at age 3 weeks, and no DS is administered. Mice are weighed and stool samples are collected twice weekly for four weeks. A blood sample is collected at age 5 weeks. After four weeks, mice are weighed, euthanized, and stool, blood, and colon samples are collected. These samples are analyzed as described below in Example 2.

The mock-treated control mice carrying a null-mutation of the IL-10 gene described in this Example are expected to show growth retardation by age 4 weeks (as evidenced by low blood hemoglobin levels), and a significant mortality incidence by 10 weeks. These mice are also expected to show clinical signs of IBD, specifically bloody fecal lactoferrin and colonic myeloperoxidase activity, perianal ulceration, and occasional rectal prolapse. Finally, these mice are expected to show histopathological signs of IBD, specifically inflammatory infiltration with lymphocytes, plasma cells, marcophages, and neutrophils, ulceration, abnormal enlarged and branched crypts, branched and fused villus structures, and marked hyperplasia of the mucosa leading to thickening of the intestinal wall. The non-IL-10 ko, calcitriol-treated, mice exhibit significantly reduced growth retardation, anemia, mortality, bloody diarrhea, intestinal inflammation, perianal ulceration and rectal prolapse, and histopathologic score as compared to the mock-treated controls.

EXAMPLE 2

Analysis of Samples from Treated Mice

This Example describes the analysis of stool, serum, and colon samples from both groups of mice described in Example 1. Stool extracts are analyzed individually for protein, hemoglobin, and lactoferrin. Serum samples are analyzed for Ca, IFN-γ, and TGF-β1. Colon samples are analyzed individually for mycloperoxidase (5/group), IFN-γ and TGF-β1 immunohistochemistry, and for histopathology (5/group). Fecal extracts and intestinal tissue extracts are assayed for protein content by a micro-Bradford assay [Bradford, M. M., Anal. Biochem., 72:248–254 (1976)]. Results of the hemoglobin, lactoferrin, and myeloperoxidase assays are then determined per mg of protein in the sample. Fecal hemoglobin and fecal lactoferrin (as well as weight) are plotted as a function of time. Histopathology scores for disease incidence and severity, myeloperoxidase activity, and IFN-γ and TGF-β1 values are tabulated, and differences between groups are compared by the nonparametric Wilcoxon test (Schefler, W. C., *Statistics for the Biological Sciences,* 2nd Edition, Addison-Wesley Pub. Co., Reading, Mass., USA, 1979).

A. Stool Sample Assays

Intestinal bleeding in a breached intestinal barrier is measured in live animals by measuring fecal hemoglobin levels, which have been shown to be elevated in UC patients [Saitoh, et al., *Digestion* 56:67–75 (1995)]. Stool samples, collected over a 24 hour period are weighed, homogenized in a small amount of water, and centrifuged in order to detect the relative hemoglobin concentration of each sample (ng/mg of protein).

The fecal hemoglobin two-site ELISA is performed on these samples as described [Saitoh, et al., *Digestion,* 56:67–75 (1995)] with modifications. All ELISA steps are separated by washing four times (TRIS-buffered saline with 0.05% Tween 20). ELISA plates (Immulon, Dynatech; 96-well) are coated overnight in the cold with rabbit polyclonal antibodies (pAb) to mouse hemoglobin (ICN Biomedical Research Products; 5 μg/ml in 0.1 M sodium carbonate buffer pH 8.2), and blocked with 0.1 M TRIS-buffered saline (pH 8) containing 1% bovine serum albumin. The samples and the hemoglobin standard (Sigma) are serially diluted in buffer (0.1 M TRIS-buffered saline, pH 7.5, with 0.1% bovine serum albumin) and aliquots are incubated 1 hour at 37° C. in duplicate assay wells; assay blank wells receive buffer only. An optimal amount of biotinylated rabbit pAb to mouse hemoglobin (ICN) is added to each well and incubated 1 hour at 37° C. The assay is developed with tetramethylbenzidine (TMB) plus hydrogen peroxide substrate solution (ICN), the reaction is stopped by adding 100 μl of 1M phosphoric acid, and the color is measured on an ELISA plate reader. The hemoglobin in each sample is determined from the linear portion of a log-linear plot of A-450 nm versus hemoglobin standard concentration, and results are expressed in ng/mg protein. The non-IL-10 ko, calcitriol-treated, mice exhibit less hemoglobin protein in stool extracts than the mock-treated control mice.

GI tract inflammation in live animals is indicated by measuring fecal lactoferrin concentrations. High levels of fecal lactoferrin have been demonstrated in patients with colorectal diseases [Sugi et al., *Am. J. Gastroenterol.* 91:927 (1996)]. The fecal lactoferrin two-site ELISA is performed in the same manner as the hemoglobin assay above, except that rabbit pAb to human lactoferrin (ICN Biomedical Research Products) replaces rabbit pAb to mouse hemoglobin as the coating Ab, and biotinylated rabbit pAb to human lactoferrin replaces rabbit pAb to mouse hemoglobin as the detecting Ab. The lactoferrin in each sample is determined from the linear portion of a log-linear plot of A-450 nm versus lactoferrin standard concentration. Results are expressed as lactoferrin ng/mg protein. The non-IL-10 ko, calcitriol-treated, mice show less lactoferrin protein in stool extracts than the mock-treated control mice.

B. Colon Tissue Assays

Large intestine of the euthenized mice are collected, and the cecum is separated from the colon. Intestinal specimens are gently flushed with Fekete's acid-alcohol-formalin fixative. The entire colon, including the rectum, is prepared as an intestinal roll [Moolenbeek and Ruitenber, *Lab Anim.* 15:57–59 (1981)]. It is placed on an index card and rolled into concentric centrifugal circles (in the plane of the card) around a central toothpick. Intestinal rolls are fixed overnight in Fekete's solution, and then transferred to 70% ethanol. The fixed intestinal rolls are then embedded in paraffin, sectioned at 5 μm, and stained with hematoxylin and eosin.

Two intestinal role sections per animal are coded and evaluated by a veterinary pathologist and a researcher without access to the code. A published evaluation method is used [Mahler et al., *Am. J. Physiol.—Gastro. & Liver Physiol.,* 37 G: 544-G 551, (1998)]. The evaluation is based on severity of lesions (graded 0 to 3), and estimated area involved (graded 0 to 4). The severity, ulceration, hyperplasia, and affected area scores are summed and tabulated, with the non-IL-10 ko, calcitriol-treated, mice exhibiting a lower histopathological score than the mock-treated mice.

Myeloperoxidase assays have been used as objective and quantitative measures of inflammation in humans [e.g. Dwarakanath et al., *Clin. Sci.* 92:307–13 (1997)] and animals [e.g. Hogaboam et al., *J. Clin. Invest.,* 100:2766–76 (1997)] with IBD. Accordingly, intestinal inflammation is measured in the mouse intestinal tissue samples by measuring myeloperoxidase activity levels. The myeloperoxidase assay is performed as in Krawisz et al., *Gastroenterol.* 87:1344–50 (1984), as modified by Schneider and Issekutz, *J. Immunol. Methods,* 198:1–14 (1996). Briefly, washed intestinal tissue samples (3/mouse; 200 mg each) are minced and homogenized in hexadecyltrimethylammonium bromide (HTAB) buffer (1 ml; 0.5% HTAB in 50 mM phosphate, pH 6) to release the enzyme. The homogenate is frozen and thawed four times, then centrifuged. The supernatant (10 μl) is added to a well of a 96-well plate containing 0.29 ml assay mix (TMB plus hydrogen peroxide substrate solution; ICN), and the A-450 nm is measured on an ELISA plate reader as a function of time. An assay blank is prepared with a heat-inactivated supernatant and subtracted. A unit of enzyme activity is defined as the amount catalyzing the oxidation of 1 μmole substrate/min under these conditions. Results are expressed as myeloperoxidase U/mg protein. The non-IL-10 ko, calcitriol-treated, mice show less myeloperoxidase protein in the intestinal tissue extracts than the mock-treated control mice.

Intestinal tissue is also analyzed for the presence of IFN-γ and TGF-β1 (cytokines thought to regulate mucosal inflammation, see below). Intestinal tissue specimens are snap frozen in OCT embedding compound (Miles Laboratories). Longitudinal 10 μm sections are applied to coated glass slides, air dried, and fixed briefly in acetone. Sections are then re-hydrated in PBS with 0.05% Tween 20, and washed in this buffer between each subsequent reaction step. All reactants are dissolved in PBS-Tween buffer. Sections are reacted 30 minutes with 3% hydrogen peroxide, then 10 minutes with 3% goat serum, then overnight in the cold with polyclonal rabbit antibodies to IFN-γ and TGF-β1 or control rabbit serum, and finally with biotinylated goat antibodies to rabbit IgG. Color is developed with the Vector Elite ABC kit. The intestinal tissue sections from the non-IL-10 ko, calcitriol-treated, mice exhibit qualitatively greater immunohistochemical staining with polyclonal rabbit antibodies to TGF-β1 and qualitatively less immunohistochemical staining with the polyclonal rabbit antibodies to IFN-γ than the intestinal tissue sections from the mock-treated control mice.

C. Blood and Serum Sample Assays

Anemia can be a sign of IBD due to blood loss in the stool. To determine whether anemia is present, 0.5 ml of blood is obtained on days 11 and 22 (prevention of DS-induced mouse IBD models) and at age 5 and 7 weeks (prevention of spontaneous mouse IBD model). A blood hemoglobin determination is performed. A small blood aliquot is dispensed into lysis buffer [3 mM $K_3(FeCN)_6$, 1.5 mM KCN, 5 mM $Na_2BO_4$, 0.1% Nonidet P-40] and the absorbance at 546 nm is measured using lysis buffer as a blank. This absorbance is compared to a reference curve produced using purified moused hemoglobin dissolved in lysis buffer. The remaining blood is allowed to clot overnight in the cold, centrifuged, and the serum is collected for further analysis.

As hypercalcemia is a possible serious side-effect of calcitriol administration [Chan et al., *Cur. Prob. Surgery*, 34:445–523 (1997)], calcitriol-treated and control mice are monitored for terminal serum calcium. Serum calcium is measured by a colormetric reaction (Sigma Diagnostics). Calcium ions form a purple complex with o-cresolphthalein complexone at alkaline pH (0.5 M 2-amino-2-methyl-1,3-propanediol buffer); 8-hydroxyquinoline (0.25%) is included to prevent magnesium ion interference. Sample, standard, or buffer blank (10 μl) is added to duplicate tubes of a working solution (1 ml) of equal parts Ca binding reagent and Ca buffer. After 5 minutes, 0.3 ml of each reaction is transferred into a 96-well plate and the absorbance at 575 nm is measured on an ELISA plate reader. Results of this assay aid in the determination the proper level and time course of calcitriol administration to avoid hypercalcemia for subjects treated for IBD with calcitriol.

In previous studies, administration of calcitriol to mice with EAE arrested the clonal expansion of Th1 cells producing IFN-γ, and stimulated TGF-β1 transcript synthesis in the central nervous system and draining lymph nodes [Cantorna et al., *J. Immunol.*, 160:5314–5319 (1998)]. Reciprocal IFN-γ and TGF-β1 responses are thought to regulate mucosal inflammation [Strober et al., *Immunol. Today*, February;18(2):61–4 (1997)], and TGF-β1 responses are crucial to suppress inflammatory colitis [Powrie et al., *J. Exp. Med.*, 183:2669–74 (1996)]. As such, a two-step ELISA is performed to analyze IFN-γ (PharMingen) and TGF-β1 (Promega Corp.) as immune response markers in the serum of the calcitriol-treated mice compared to mock-treated mice.

EXAMPLE 3

Treating Established IBD in Mice

This example describes the treatment of established IBD in mice using calcitriol. The procedure is the same as Example 1 above, except treatment is not started until the mice show signs of IBD. This is accomplished by administering DS in the drinking water of the mice listed in groups 1–4 in Table 1, followed by acidified water without DS thereafter. The mice are also weighed at the beginning of this procedure. At two-day intervals, stool samples are tested as in Example 1 for hemoglobin and lactoferrin. Treatment with calcitriol is begun when these test indicate the mice are suffering from IBD.

Thereafter, weights and stool samples are obtained at 4-day intervals. On day 22, the mice are weighed, euthanized, and stool, blood, and colon samples are collected. Stool extracts, blood, serum, and colon samples are analyzed as described in above in Example 2. Weight, fecal and blood hemoglobin, and fecal lactoferrin are plotted as a function of time. Disease incidence, severity (as evidenced by histopathologic score), myeloperoxidase activity, and IFN-γ and TGF-β1 values are then tabulated. The results of this experiment indicate that calcitriol treatment of mice exhibiting symptoms of IBD exhibit reduced symptoms of disease compared to controls.

EXAMPLE 4

Therapeutic and Prophylactic Use of Calcitriol to Treat and Prevent IBD

Therapeutic formulations of calcitriol are used prophylactically and therapeutically to treat IBD in humans. Individuals at risk of contracting IBD, particularly young adults, or those or Jewish descent are administered an effective amount of calcitriol in a therapeutic formulation to prevent or reduce the severity of the disease. A patient with symptoms of IBD is administered an effective dose of calcitriol daily until symptoms of IBD are reduced.

EXAMPLE 5

Therapeutic and Prophylactic Use of Vitamin D to Treat and Prevent IBD

Therapeutic formulations of vitamin D are used prophylactically and therapeutically to treat IBD in humans. Individuals at risk of contracting IBD, particularly young adults, or those or Jewish descent are administered an effective amount of vitamin D in a therapeutic formulation to prevent or reduce the severity of the disease. A patient with symptoms of IBD is administered an effective dose of vitamin D daily until symptoms of IBD are reduced.

EXAMPLE 6

DS-Induced Animal Model of Ulcerative Colitis

This Example describes the generation of a mouse model for dextran sulfate (DS) induced colitis. This DS-induced colitis model was adapted from Okayasu et al. (1990) for use with a synthetic diet. In this Example, male C3H/HeJ mice were used, as these mice are highly susceptible to DS-induced colitis. Initially, mice were given 3.5% DS w/v in acidified water for 5 days, followed by acidified water without DS, and continuously fed a synthetic diet (synthetic diet described in Smith and Hayes, *PNAS*, USA, 84:5878–5882, 1987). These mice showed no signs of colitis (e.g., diarrhea, blood in the stool, weight loss). These mice shunned the water containing DS, and met their hydration needs by consuming the synthetic diet (which is approximately 60% water by weight). A second group of mice were given 3.5% DS w/v in acidified water for 5 days, followed by acidified water without DS, and continuously fed laboratory chow (Purina mouse chow #5008) as described in Mahler et al., *Gastrointest, Liver Physiol.*, 37:G544–G551 (1996). These mice, consuming an average of 0.57 g DS/mouse, lost weight (controls 26.1±0.7 g; DS group 22.8±0.3 g), and had hemoglobin (Hg) in the stool (controls 0±0 mg Hg/g stool; DS group 11.4 mg Hg/g stool). These results indicate the colitis was induced in this group as expected.

To adapt the DS-induced model for use with the synthetic diet (see Smith and Hayes, 1987), a third group of mice were given graded amounts of DS in acidified water and a synthetic diet for 5 days, followed by acidified water and the synthetic diet without DS. These mice were weighed twice weekly and subjected to various other assays, including: fecal hemoglobin analysis, and histopathologic analysis. The results are presented below in Tables 2 and 3.

A. Fecal Hemoglobin Analysis

Fecal hemoglobin was analyzed in the mice to determine bleeding from a breached intestinal barrier. Fresh stool samples were collected from individual mice, dried overnight, weighed, and suspended in 0.5 mL of TRIS-buffered saline (TBS; 25 mM TRIS, 0.15 M NaCl, pH 7.6). The stool samples were centrifuged (10,000×g for 10 min) at room temperature in a Micromax centrifuge (International Equip. Co., Needham Heights, Mass.), the supernatants were decanted into fresh tubes and stored frozen at −20° C. Hemoglobin in the supernatants was analyzed by a method adapted from Saitoh et al., *Digestion*, 56:67–75, 1995, and Liem et al., *Anal. Biochem.*, 98:388–393, 1979, with rat hemoglobin as standard (Sigma-Aldrich). The supernatants were diluted 1:25 in TBS. The assay was done in round-bottom, polystyrene, 96 well microtiterplates (#3555, DYNEX Technologies, Chantily, Va.). The samples, standards, and buffer blanks (20 µL each) were incubated in duplicate for 10 min with 100 µL of a substrate solution made with 9 volumes 3,3'5,5'-tetramethylbenzidine dihydrochloride peroxide solution (Turbo TMB-ELISA, Pierce Chemical Co., Rockford, Ill.) and 1 volume of hydrogen peroxide solution (Stable Peroxide Substrate Buffer, Pierce Chemical Co.). The reaction was stopped with 100 µL of 2 M phosphoric acid, and the absorbance at 450 nm was measured with an MRX Revelation Microplate Reader (DYNEX Technologies). The fecal hemoglobin assay working range was 1 to 100 µg/mL sample. The hemoglobin mg/g stool was calculated and reported in Table 3.

B. Histopathologic Analysis

The mice were euthanized with an i.p. injection of pentobarbital. The cecal and rectal GI tract segments were collected, cut longitudinally, flushed with 10% neutral-buffered formalin, arranged in a spiral pattern in a cassette, and fixed in formalin. The fixed tissue was embedded in paraffin, sectioned at 6 µm, stained with hematoxylin and eosin, and examined by light microscopy. Scoring was conducted by a veterinary pathologist in blinded fashion. Each colon segment (proximal, medial, and distal colon, and rectum) was given a score from 0 to 4, based on the criteria described by Berg et al., *J. Clin. Invest.*, 98:1010–1020, 1996. The scores were summed to provide a total colitis score for each mouse. The total colitis score could range from 0 (no pathology in any segment) to 16 (grade 4 lesions in all colon segments).

TABLE 2

Weight Change and Mortality in DS-Induced Mice

| Group (No. of mice) | DS given[a] (%) | DS consumed (grams) | Weight change (%, day 0–11) | Mortality (%) |
|---|---|---|---|---|
| A (2) | 0 | 0 | 8.2 ± 0.2 | 0 |
| B (3) | 1 | 0.64 | 2.1 ± 0.9 | 0 |
| C (3) | 1.5 | 0.89 | −12.4 ± 0.7 | 66 |
| D (3) | 2.0 | 1.07 | −17.5 ± 0.2[b] | 100 |
| E (3) | 3.0 | 0.80 | −5.4 | 0 |

[a]DS was fed on days 0 to 5. All groups except E were fed synthetic diets. For groups B, C, and D, the DS was in the acidified drinking water and in the synthetic diet. For group, E, the DS was in the drinking water and the mice were fed laboratory chow.
[b]Weight change day 0 to 6, when mortality reached 100%.

TABLE 3

Fecal Hg and Colitis Severity in DS-Induced Mice

| Group (No. of mice) | DS given[a] (%) | Peak Hg in Stool (mg/g) | Colon Histopathology (sum) |
|---|---|---|---|
| A (2) | 0 | 0 | 0.5 ± 0.7 |
| B (3) | 1 | 1.8 | 6.3 ± 3.5 |
| C (3) | 1.5 | 16.7 | 6.5 |
| D (3) | 2.0 | 31.7 | nd |
| E (3) | 3.0 | 11.4 | 9.5 ± 0.9 |

[a]The experiment was done as described in Table 2 footnote.

In this third group of mice, weight loss (Table 2) and fecal Hg values (Table 3) were proportional to the amount of DS ingested, with fecal Hg peaking on day 5 of DS administration. Further, the total colitis score was proportional to the amount of DS ingested (Table 3). The concentration of 1% DS in food and water was selected for further analysis as it minimized mortality (which was substantial in the higher DS groups, see Table 2), and gave colon histopathology scores that were not significantly different from those achieved with the Okayasu et al. (1990) method.

EXAMPLE 7

Calcitriol Prevention of DS-Induced Colitis

This Example demonstrates the ability of calcitriol to prevent colitis in DS-induced mouse models of colitis. In particular, age-matched C3H/HeJ male mice were fed a synthetic diet (see Example 6) with or without calcitriol or prednisolone for one week. The drug treatments were continued, and IBD was induced with a 5 day administration of 1% DS in the food and water as described in Example 6. The mice were weighed every 3–4 days thereafter. Fecal Hg was analyzed daily from day 3 to day 7. Serum and colon tissue were collected on day 28. Most assays were performed as described in Example 6, and the terminal serum calcium assay was performed as described below. The results are reported in Tables 4 and 5.

In order to determine serum calcium, blood was collected, allowed to clot, and centrifuged (5,000×g for 10 minutes) at 6° C. The serum was decanted and stored frozen at −20° C. The samples, standards, and buffer blanks (2 µL each) were aliquoted into duplicate wells of a 96-well plate. Calcium reagent working solution (0.25 mL), prepared according to the manufacturer's directions (Sigma Diagnostics, St. Louis, Mo.), was added to each well, and the absorbance at 570 nm was measured. The $Ca^{++}$ mg/dL serum was calculated and reported in Table 4.

TABLE 4

Calcitriol Prevention of IBD in Mice - Fecal Hg, Serum Calcium, and Weight

| Group | Dextran Sulfate %[a] | Treatment[b] | Peak Hg in stool (mg/g) | Terminal serum $Ca^{++}$ mg/dL | Terminal weight (g) |
|---|---|---|---|---|---|
| A | 0 | 0 | 0 ± 0 | 10.0 ± 1.4 | 31.0 ± 2.9 |
| B | 1 | 0 | 6.8 ± 1.6 | 8.8 ± 1.9 | 28.9 ± 3.7 |
| C | 1 | Calcitriol 50 ng/day | 4.3 ± 4.4 | 11.2 ± 2.1 | 28.0 ± 2.9 |
| D | 1 | Prednisolone 50 ng/day | 12.3 ± 10.0 | 10.5 ± 1.2 | 29.4 ± 1.4 |

[a]All groups (A, B, and C, n = 12; D, n = 7) were fed synthetic diet beginning one week before DS treatment (day −7). DS was fed on days 0 to 5 in the acidified drinking water and in the diet. The experiment was terminated on day 27.
[b]Hormones were fed continuously in the diet beginning one week before DS treatment (day −7).

The results (presented in Tables 4 and 5) indicate that calcitriol pre-treatment reduced the severity of DS-induced IBD. The DS-treated animals weighed slightly less than the untreated control (Table 4), and the incidence of IBD in these animals was 100%, as judged by colon histopathology, regardless of the treatment method. Importantly, the peak Hg in the stool of the calcitriol-treated group was 37% lower than that in the untreated group, and 65% lower than that in the prednisolone-treated group. In addition, the total colon histopathology score of the calcitriol-treated group C was 61% lower than the score of the untreated group B, and 51% lower than the score of the prednisolone-treated group D (Table 5). These results show that calcitriol pre-treatment was more effective than prednisolone in reducing DS-induced IBD severity.

EXAMPLE 8

Calcitriol Treatment of Chronic DS-Induced Colitis

This Example demonstrates the ability of calcitriol to treat chronic colitis in DS-induced mouse models of colitis. In particular, age-matched adult C3H/HeJ male mice were subjected to three DS treatment cycles treatment separated by 6–8 weeks. Each DS treatment was a 5-day administration of 1% DS in acidified water and in synthetic diet. Between treatments, the mice were fed laboratory mouse chow. These treatments induced chronic IBD. Beginning 10 days after the last DS treatment was completed, the mice were divided into two groups. The groups were matched with respect to fecal Hg and weight (Table 6). Group A was fed synthetic diet and group B was fed calcitriol in synthetic diet. The experiment was terminated 21 days later. The colon histopathology results indicate that calcitriol treatment reduced the severity of chronic DS-induced IBD. In particular, the mice treated with calcitriol for 21 days had an approximately 45% reduction in colon histopathology (Table 7).

TABLE 6

Calcitriol Treatment of Chronic DS-Induced IBD in Mice

| Group | Dextran-Sulfate | Treatment | Hemoglobin in Stool (DS cycle 3) mg/g | Terminal serum Calcium mg/dL | Terminal weight (g) |
|---|---|---|---|---|---|
| A | 3 cycles of 1% | none | 12 ± 8 | 8.9 ± 0.6 | 37.9 ± 4.4 |

TABLE 5

Calcitriol Prevention of IBD in Mice - Colon Histopathology

| Group | DS[a] % | Treatment | Proximal colon | Medial Colon | Distal Colon | Rectum | Sum |
|---|---|---|---|---|---|---|---|
| A | 0 | 0 | 0 ± 0 | 0 ± 0 | 0 ± 0 | 0.2 ± 0.3 | 0.2 ± 0.3 |
| B | 1 | 0 | 2.0 ± 1.4 | 0.8 ± 0.8 | 1.8 ± 2.0 | 2.0 ± 2.0 | 6.6 ± 5.1 |
| C | 1 | Calcitriol 50 ng/day | 0.4 ± 0.5 | 0.4 ± 0.9 | 0.6 ± 0.9 | 1.2 ± 1.1 | 2.6 ± 1.9 |
| D | 1 | Prednisolone 50 ng/day | 1.0 ± 0 | 0.3 ± 0.5 | 1.1 ± 0.4 | 2.9 ± 1.1 | 5.3 ± 1.4 |

[a]The experiment was done as described in the Table 4 legend.
[b]Colons were collected, fixed, embedded, stained, and scored by a veterinary pathologist as described in Example 6.

TABLE 6-continued

Calcitriol Treatment of Chronic DS-Induced IBD in Mice

| Group | Dextran-Sulfate | Treatment | Hemoglobin in Stool (DS cycle 3) mg/g | Terminal serum Calcium mg/dL | Terminal weight (g) |
|---|---|---|---|---|---|
| B | 3 cycles of 1% | Calcitriol (50 ng/day after cycle 3) | 9 ± 10 | 10.3 ± 1.1 | 35.1 ± 4.0 |

TABLE 7

Calcitriol Treatment of Chronic DS-Induced IBD in Mice - Colon Histopathology

| Group | DS (%) | Treatment | Proximal colon | Medial colon | Distal colon | Rectum | Sum |
|---|---|---|---|---|---|---|---|
| A | 3 cycles of 1% | none | 3 ± 1 | 2 ± 1 | 2 ± 1 | 4 ± 1 | 11 ± 2 |
| B | 3 cycles of 1% | Calcitriol 50 ng/day after cycle 3. | 2 ± 1 | 1 ± 1 | 1 ± 1 | 2 ± 1 | 6 ± 2 |

Colons were collected, fixed, embedded, stained, and scored by a veterinary pathologist as described in Example 6.

EXAMPLE 9

Spontaneous Colitis in Strain 129-IL-10-Deficient Mice

This example describes the spontaneous colitis that develops spontaneously in strain 129-IL-10$^{-/-}$ mice with and without administration of calcitriol. It has been reported that mice made genetically deficient in IL-10 spontaneously develop chronic enterocolitis (Kuhn et al., *Cell*, 75:263–274, 1993) if resident enteric bacteria is present (Sellon et al., *Infect. Immunity*, 66:5224–5231, 1998). The effect of calcitriol on spontaneous colitis in 129-IL-10$^{-/-}$ mice is examined. Mice raised in gnotobiotic conditions were transferred to conventional conditions and fed synthetic diet with and without graded doses of calcitriol. The mice were age 7 weeks when they were exposed to soiled bedding from mice housed under conventional conditions. This was done to provide the enteric bacteria for development of colitis.

The results (presented in Table 8 and Table 9) indicate that calcitriol did not prevent spontaneous colitis in the 129-IL-10$^{-/-}$ mice. The calcitriol-treated mice had a lower terminal weight than the mock-treated mice (Table 8). The calcitriol-treated mice developed hypercalcemia (Table 8), indicating that they are capable of responding to calcitriol treatment as regards Ca absorption. However, the calcitriol-treated mice had colitis histopathology scores equal to the mock-treated mice (Table 9), indicating that calcitriol treatment had no effect on spontaneous colitis in strain 129-IL-10$^{-/-}$ mice.

TABLE 8

Calcitriol Treatment of 129-IL-10$^{-/-}$ Mice

| Group | Treatment | Peak hemoglobin in stool | Terminal serum calcium (mg/dL) | Terminal Weight (g) |
|---|---|---|---|---|
| A | 0 | 0 ± 0 | 8.2 ± 0.6 | 24.1 ± 0.7 |
| B | Calcitriol (10 ng/day) | 0 ± 0 | 12.5 ± 1.5 | 19.5 ± 1.5 |

TABLE 9

Calcitriol Treatment of 129-IL-10$^{-/-}$ - Colon Histopathology

| Group | Treatment | Proximal colon | Medial colon | Distal colon | Rectum | Sum |
|---|---|---|---|---|---|---|
| A | 0 | 4 ± 0 | 4 ± 0 | 4 ± 0 | 4 ± 0 | 16 ± 0 |
| B | Calcitriol 10 ng/day | 4 ± 0 | 4 ± 0 | 4 ± 0 | 4 ± 0 | 16 ± 0 |

EXAMPLE 10

Treatment of IBD in an IL-10 Deficient Subject

This Example describes the treatment of a subject that is IL-10 deficient and suffering from IBD. A human subject with symptoms of IBD is screened for the presence of IL-10 and determined to be IL-10 deficient. Next, the subject is administered a therapeutic formulation (daily) that includes approximately 7 micrograms of calcitriol and approximately 8 micrograms/kg of IL-10 in order to prevent or reduce the severity of the symptoms of IBD. This therapeutic formulation is administered daily until symptoms of IBD are reduced or eliminated.

EXAMPLE 11

Treatment of Spontaneous Colitis in B6×129-IL-10-$^{-/-}$ Mice

This example describes the treatment of spontaneous colitis in B6×129-IL-10-$^{-/-}$ mice with 1,25-(OH)$_2$D$_3$ (i.e. calcitriol). Adult B6×129-IL-10-$^{-/-}$ mice were transferred from gnotobiotic to conventional housing conditions and colonized with enteric bacteria from conventional, pathogen-free mice (it has been previously reported that *Helicobacter* species trigger colitis in IL-10$^{-/-}$ mice, see Kullberg et al., *Infect. Immun.* 66:5157–66, 1998. Stool samples were tested for *Helicobacter* species and found to be negative.

Figure 3:
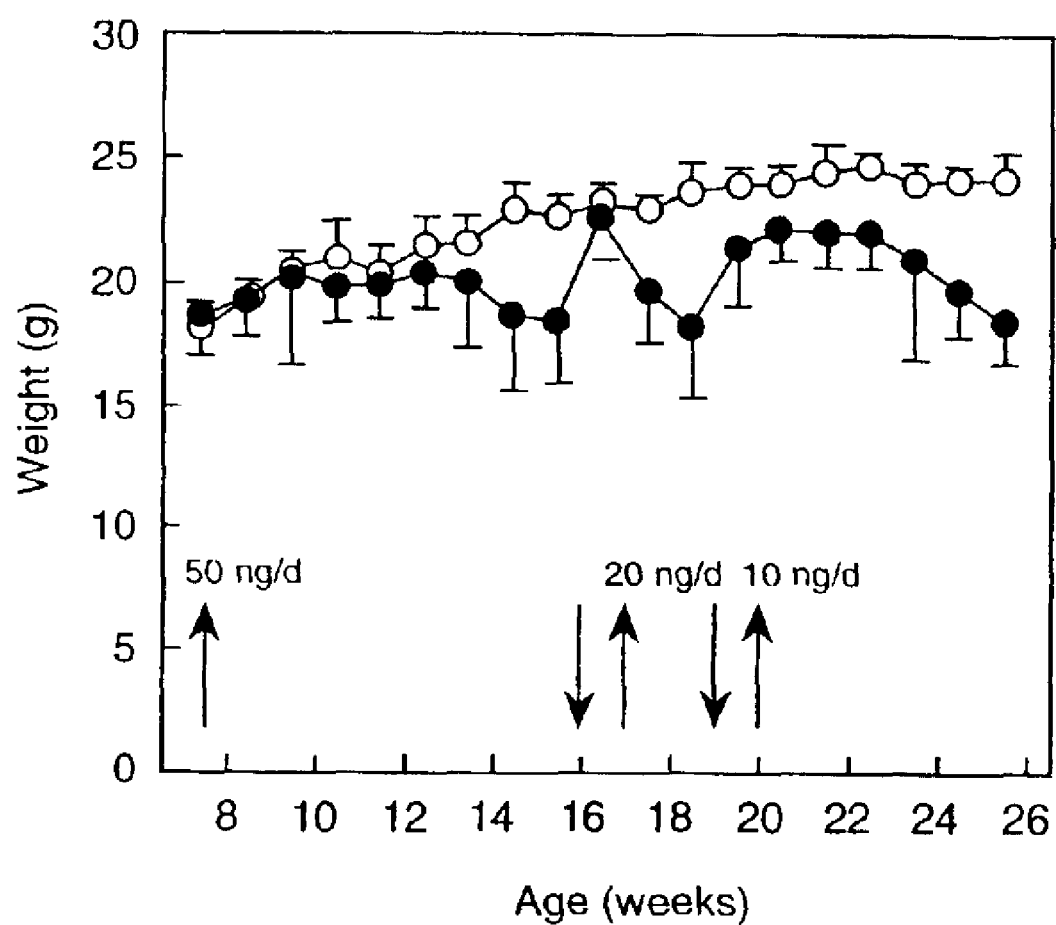
FIG. 3 shows the weight of B6×129-IL-10$^{-/-}$ mice treated with calcitriol (filled in circles) and without calcitriol (open circles).

The B6×129-IL-10-$^{-/-}$ male and female mice were fed synthetic diet with calcitriol (FIG. 3, filled in circles) and without calcitriol (FIG. 3, open circles) beginning at the time of enteric bacteria colonization. The mice that ingested calcitriol (50 ng/d for females; 100 ng/d for males) from age 7 weeks gained weight to age 14 weeks, then lost about 15% of their weight (FIG. 3). The male mice died abruptly at age 15 weeks. Serum calcium analysis on the remaining female mice indicated that they were hypercalcemic (Table 10), so calcitriol feeding was discontinued for one week, whereupon their weight returned to normal. The calcitriol feeding was resumed at a lower dose (20 ng/d) at age 16 weeks. The mice again lost 15% of their weight and were hypercalcemic (Table 10), so calcitriol feeding was discontinued for one week. The calcitriol feeding was resumed at a lower dose (10 ng/d) at age 18 weeks. The mice lost weight and became hypercalcemic at this dose (Table 10).

TABLE 10

Hypercalcemia in Calcitriol Treated B6x129-IL-10$^{-/-}$

| Calcitriol treatment (ng/d) | Serum Calcium C3H/HeJ male[a] (mg/dL) | Serum Calcium 129x1/SvJ male[a] (mg/dL) | Serum Calcium B6x129-IL-10$^{-/-}$ male[b] (mg/dL) | Serum Calcium B6x129-IL-10$^{-/-}$ female[b] (mg/dL) |
|---|---|---|---|---|
| 0 | 9.5 ± 1.3 | 8.3 ± 1.3 | 13.5 ± 3.5 | 9.4 ± 1.1 |
| 10 | 10.5 ± 2.1 | 12.4 ± 0.6 | 15.8 ± 2.1 | 12.5 ± 1.5 |
| 20 | 10.1 ± 2.7 | 11.5 ± 0.1 | 14.4 ± 1.0 | 13.0 ± 3.0 |
| 50 | 9.9 ± 0.6 | 11.5 ± 0.4 | 16.0 ± 3.5 | 12.9 ± 2.4 |
| 100 | 10.1 ± 1.8 | 11.1 ± 1.1 | nd | nd |

[a]The C3H/HeJ and 129x1/SvJ mice were treated with the same calcitriol dose for two weeks, and serum calcium was analyzed; nd, not determined.
[b]The female B6x129-IL-10$^{-/-}$ mice were treated with calcitriol as shown in FIG. 3. The serum calcium was analyzed each time the mice lost 15% of body weight. In a separate study, male B6x129-IL-10$^{-/-}$ mice were treated with graded calcitriol doses and the serum calcium was analyzed four weeks later.

In a further study, male B6x129-IL-10$^{-/-}$ mice were fed synthetic diet with and without graded doses of calcitriol beginning at age 7 weeks. Four weeks later, the serum calcium levels were measured (Table 10). The control B6x129-IL-10$^{-/-}$ mice had a slightly elevated serum calcium level compared to the C3H/HeJ mice. However, the B6x129-IL-10$^{-/-}$ mice ingesting even very low doses of calcitriol had severe hypercalcemia. These calcitriol doses were well tolerated by male C3H/HeJ mice with and without colitis, and by male 129x1/SvJ mice (See Table 10).

The finding of severe hypercalcemia in calcitriol treated B6x129-IL-10$^{-/-}$ mice indicated that this mouse strain was capable of responding to the hormone. Remarkably, however, the calcitriol treatment did not inhibit spontaneous colitis in the B6x129-IL-10$^{-/-}$ mice. The colitis severity scores of the mock-treated and hormone-treated (50 ng/d) mice were not significantly different (Table 11).

TABLE 11

Effect of Calcitriol Treatment on Spontaneous Colitis in B6x129-IL-10$^{-/-}$ mice

| Characteristic[a] | Group A | Group B | Group C | Group D |
|---|---|---|---|---|
| Sex | female | male | female | male |
| Treatment | none | none | calcitriol | calcitriol |
| Peak fecal hemoglobin (mg/g) | 0 ± 0 | 0 ± 0 | 0 ± 0 | 0 ± 0 |
| Terminal Serum Ca (mg/dL) | 8.6 ± 0.7 | 9.9 ± 0.2 | 12.5 ± 1.5 | 15.6 ± 2.5 |
| Terminal weight (g) | 24.1 ± 0.7 | 29.4 ± 2.8 | 19.5 ± 1.5 | 19.7 ± 0.9 |
| Colon Histopathology[b] | — | — | — | — |
| Proximal colon | 4.0 ± 0.0 | 4.0 ± 0.0 | 3.9 ± 0.3 | 3.7 ± 0.6 |
| Middle colon | 3.0 ± 0.0 | 3.0 ± 0.0 | 3.3 ± 0.5 | 1.7 ± 1.2 |
| Distal colon | 4.0 ± 0.0 | 3.3 ± 0.5 | 3.3 ± 0.5 | 3.0 ± 0.0 |
| Rectum + anus | 3.7 ± 0.6 | 3.0 ± 2.0 | 2.8 ± 1.9 | 2.7 ± 0.6 |
| Sum | 14.7 ± 0.6 | 13.3 ± 2.2 | 13.1 ± 2.7 | 11.1 ± 1.0 |

[a]The female mice were treated with calcitriol beginning at the time enteric bacteria were introduced (age 7 weeks), and the dose was gradually reduced as shown in FIG. 3. The experiment was terminated when the mice were age 24 weeks. In a separate experiment, male mice were treated with graded calcitriol doses beginning at age 7 weeks, and the experiment was terminated when the mice were age 19 weeks. The data shown are for males treated with 50 ng/d of calcitriol.
[b]Colon samples were prepared and scored by A.G.F. as described in Berg et al., J. Clin. Invest., 98: 1010–20 (1996). The values shown are the mean and SD for four mice per group.

The B6x129-IL-10$^{-/-}$ mice did not exhibit hemoglobin in the stool or anemia. The 129x1/SvJ strain is genetically similar to the 129/Ola strain and to the 129/SvPas strain, which is less susceptible to DSS-induced colitis than C3H/HeJ. To study whether calcitriol treatment reduces colitis in strain 129x1/SvJ mice, groups of male mice were given DSS to induce colitis, and treatment was started when hemoglobin was first detected in the stool (Table 12).

TABLE 12

Effect of Calcitriol Treatment at the First Signs of Colitis in 129X1/SvJ Mice

| Characteristic[a] | Group A | Group B | Group C | Group D |
|---|---|---|---|---|
| DSS (1%)[a] | none | 1 cycle | 1 cycle | 1 cycle |
| Treatment | none | none | calcitriol | prednisolone |
| Peak fecal hemoglobin (mg/g) | 0.4 ± 0.6 | 0.7 ± 0.3 | 1.3 ± 1.2 | 0.4 ± 0.6 |
| Terminal Serum Ca (mg/dL) | 8.3 ± 1.3 | 8.7 ± 1.5 | 9.7 ± 3.2 | 8.3 ± 1.3 |
| Terminal weight (g) | 26.9 ± 1.4 | 27.1 ± 1.4 | 26.4 ± 3.3 | 26.5 ± 02.0 |
| Colon Histopathology[b] | — | — | — | — |
| Proximal colon | 0.2 ± 0.4 | 1.0 ± 0.6 | 0.4 ± 0.8 | 0.7 ± 0.4 |
| Middle colon | 0 ± 0 | 0.7 ± 0.5 | 0 ± 0 | 0.2 ± 0.3 |
| Distal colon | 0 ± 0 | 0.7 ± 0.5 | 0.6 ± 0.9 | 2.0 ± 0.3 |
| Rectum + anus | 0 ± 0 | 0.2 ± 0.4 | 0.2 ± 0.4 | 0.8 ± 1.1 |
| Sum | 0.2 ± 0.4 | 2.5 ± 1.5 | 1.2 ± 1.8 | 3.7 ± 1.3 |

[a]Groups of six adult mice were given 1% DSS in the synthetic diet and in the water on days 0 to 5. Control mice received no DSS. On day 4 of DSS administration, when fecal hemoglobin was first detected in the stool, the treatments were started. The group C received calcitriol (50 ng/d), and the group D mice received prednisolone (50 ng/d). The experiment was terminated 21 days later.
[b]Colon samples were prepared and scored by A.G.F. as described in Berg et al., J. Clin. Invest., 98:1010–20 (1996). The values shown are the mean and SD for four mice per group.

Three weeks later, the calcitriol-treated mice had a significant reduction in colon histopathology compared to the mock-treated mice and prednisolone-treated mice, and none of the groups showed hypercalcemia. Thus, in contrast to the beneficial effects of calcitriol in the DSS-induced colitis mode in C3H/HeHJ and 129x1/SvJ mice, the data shows that the calcitriol did not reduce spontaneous colitis in the B6x129-IL-10$^{-/-}$ mice, and in these animals, particularly in males, the hormone treatment induced severe hypercalcemia.

EXAMPLE 12

Vitamin D Treatment Protocol

This example describes a vitamin D treatment protocol to provide the benefits of hormone treatment while avoiding the negative consequences of long-term hormone treatment. In particular, a subject (e.g. human) is first administered for a short period (e.g. 1 week to 1 month) 1α-hydroxyvitamin D3. This is followed by a longer period (e.g. 1 year to life-long) of treatment with the precursor vitamin D3 (also known as cholecalciferol) at about 2000 IU/day to about 4000 IU/day.

All publications and patents mentioned in the above specification are herein incorporated by reference. Various modifications and variations of the described method and system of the invention will be apparent to those skilled in the art without departing from the scope and spirit of the invention. Although the invention has been described in connection with certain preferred embodiments, it should be understood that the invention as claimed should not be unduly limited to such embodiments. Indeed, various modifications of the described modes for carrying out the invention which are obvious to those skilled in bio-chemistry, immunology, chemistry, molecular biology, the medical profession or related fields are intended to be within the scope of the following claims.

What is claimed is:

1. A method of treatment, comprising:
    administering a therapeutically effective amount of a biologically active vitamin D compound selected from 1,25-dihydroxyvitamin $D_3$ or 1α-hydroxyvitamin $D_3$, and a therapeutically effective amount of interleukin-10 to a subject with symptoms of a vitamin D responsive disease, wherein said vitamin D responsive disease is selected from the group consisting of osteoporosis, renal osteodystrophy, psoriasis, multiple sclerosis, arthritis, ulcerative colitis, and Crohn's disease.

2. The method of claim 1, wherein said administration does not cause severe or moderate hypercalcemia.

3. The method of claim 1, further comprising determining if said subject is an IL-10 deficient subject.

4. The method of claim 1, wherein said at least one vitamin D responsive disease is selected from the group consisting of osteoporosis, renal osteodystrophy, psoriasis, multiple sclerosis, and arthritis.

5. The method of claim 1, wherein said vitamin D responsive disease is ulcerative colitis or Crohn's disease.

6. The method of claim 1, wherein said interleukin-10 is human.

7. The method of claim 1, wherein said interleukin-10 is recombinant.

8. The method of claim 1, wherein said biologically active vitamin D compound is 1,25-dihydroxyvitamin $D_3$.

9. The method of claim 1, wherein said biologically active vitamin D compound is 1α-hydroxyvitamin $D_3$.

10. The method of claim 1, wherein said administering is via a transdermal patch.

11. The method of claim 1, wherein said therapeutically effective amount of said biologically active vitamin D compound comprises a daily dose of at least 5 µg per day.

12. The method of claim 1, wherein said therapeutically effective amount of said interleukin-10 comprises a daily dose of approximately 4–6 µg per kilogram of said subject per day.

13. A composition comprising a first amount of a biologically active vitamin D compound selected from 1,25-dihydroxyvitamin $D_3$ or 1α-hydroxyvitamin $D_3$, and a second amount of interleukin-10, wherein said first amount is between 0.01 µg and 50 µg, and wherein said second amount is between 25 µg and 500 µg.

14. The composition of claim 13, wherein said first amount is between 0.1 µg and 25 µg.

15. The composition of claim 13, wherein said second amount is between 175 µg–400 µg.

16. The composition of claim 13, wherein said second amount is between 250 µg–350 µg.

17. The composition of claim 13, wherein said interleukin-10 is human.

18. The composition of claim 13, wherein said interleukin-10 is recombinant.

19. The composition of claim 13, wherein said biologically active vitamin D compound is 1,25-dihydroxyvitamin $D_3$.

20. The composition of claim 13, wherein said biologically active vitamin D compound is 1α-hydroxyvitamin $D_3$.

* * * * *

UNITED STATES PATENT AND TRADEMARK OFFICE
CERTIFICATE OF CORRECTION

| | |
|---|---|
| PATENT NO. | : 6,989,377 B2 |
| APPLICATION NO. | : 10/170746 |
| DATED | : January 24, 2006 |
| INVENTOR(S) | : Colleen E. Hayes and Faye E. Nashold |

It is certified that error appears in the above-identified patent and that said Letters Patent is hereby corrected as shown below:

Page 2, Col. 2, line 53: For Lemire, J. M. et al., in the title, delete "Protolongation" and replace it with --Prolongation--.

Page 3, Col. 2, line 34: For Schneider, T. et al., in the title, delete "Quantiation" and replace it with --Quantitation--.

Page 4, Col. 1, line 47: For Asou, H. et al., after "Oct. 1, (1998)" add the phrase --; published by The American Society of Hematology.--.

Page 4, Col. 1, line 55: Delete "Cantoma, M. T. et al." and replace it with --Cantorna, M. T. et al.--.

Page 4, Col. 1, line 60: Delete "Cantoma, M. T. et al." and replace it with --Cantorna, M. T. et al.--.

Page 4, Col. 2, line 1: Delete "Cantoma, M. T. et al." and replace it with --Cantorna, M. T. et al.--.

Page 4, Col. 2, line 54: Delete "Cantoma, M. T. et al." and replace it with --Cantorna, M. T. et al.--.

Col. 1, lines 5-6: Delete the words "and is a Continuation-in-part of and".

Col. 2, line 12: Delete the phrase "is better then that of full colon UC." and replace it with --is better than that of full colon UC.--.

Col. 3, line 30: Delete the phrase "administered to the subjected" and replace it with --administered to the subject--.

Col. 23, lines 61-62: Delete the phrase "biologically active vitamin D compound are used" and replace it with --biologically active vitamin D compounds are used--.

Col. 26, line 39: Delete the phrase "subject that are known (or determined to be)" and replace it with --subjects that are known (or determined to be)--.

Col. 31, line 59: Delete the phrase "aid in the determination the proper level" and replace it with --aid in the determination of the proper level--.

UNITED STATES PATENT AND TRADEMARK OFFICE
CERTIFICATE OF CORRECTION

PATENT NO. : 6,989,377 B2
APPLICATION NO. : 10/170746
DATED : January 24, 2006
INVENTOR(S) : Colleen E. Hayes and Faye E. Nashold It is certified that error appears in the above-identified patent and that said Letters Patent is hereby corrected as shown below:

Col. 32, line 22: Delete the phrase "these test indicate" and replace it with --these tests indicate--.

Col. 32, line 28: Delete the phrase "as described in above in Example 2." and replace it with --as described above in Example 2.--.

Col. 32, line 44: Delete the phrase "or those or Jewish descent" and replace it with --or those of Jewish descent--.

Col. 32, line 57: Delete the phrase "or those or Jewish descent" and replace it with --or those of Jewish descent--.

Col. 36, lines 24-25: Delete the phrase "to three DS treatment cycles treatment separated by 6-8 weeks." and replace it with --to three DS treatment cycles separated by 6-8 weeks.--.

Signed and Sealed this

Twenty-sixth Day of December, 2006

JON W. DUDAS
*Director of the United States Patent and Trademark Office*